(12) United States Patent
Reid et al.

(10) Patent No.: US 8,222,210 B2
(45) Date of Patent: Jul. 17, 2012

(54) METHODS OF USING SUBSTANCE P TO PROMOTE HEALING OF VASCULAR WOUNDS

(76) Inventors: Ted Reid, Lubbuck, TX (US); Christopher J. Murphy, Madison, WI (US)

( * ) Notice: Subject to any disclaimer, the term of this patent is extended or adjusted under 35 U.S.C. 154(b) by 0 days.

(21) Appl. No.: 12/556,402

(22) Filed: Sep. 9, 2009

(65) Prior Publication Data

US 2010/0092561 A1 Apr. 15, 2010

Related U.S. Application Data

(63) Continuation of application No. 11/603,541, filed on Nov. 21, 2006, now abandoned.

(60) Provisional application No. 60/738,910, filed on Nov. 22, 2005, provisional application No. 60/739,154, filed on Nov. 22, 2005, provisional application No. 60/740,489, filed on Nov. 28, 2005.

(51) Int. Cl.
*A61K 38/00* (2006.01)
*A61K 9/14* (2006.01)
*A61K 31/715* (2006.01)
*A61P 17/02* (2006.01)
*A01N 43/04* (2006.01)

(52) U.S. Cl. ............ 514/9.4; 424/486; 424/488; 514/54

(58) Field of Classification Search .................. None
See application file for complete search history.

(56) References Cited

U.S. PATENT DOCUMENTS

| | | | |
|---|---|---|---|
| 5,314,690 A | 5/1994 | Patterson et al. | |
| 5,410,019 A | 4/1995 | Coy et al. | |
| 5,545,617 A | 8/1996 | Dartt et al. | |
| 5,604,198 A | 2/1997 | Poduslo et al. | |
| 5,616,562 A | 4/1997 | Murphy et al. | |
| 5,624,893 A | 4/1997 | Yanni | |
| 5,744,156 A | 4/1998 | De Lacharriere et al. | |
| 5,824,650 A | 10/1998 | De Lacharriere et al. | |
| 5,866,168 A | 2/1999 | De Lacharriere et al. | |
| 5,945,508 A | 8/1999 | Witten et al. | |
| 5,972,892 A | 10/1999 | De Lacharriere et al. | |
| 5,998,376 A | 12/1999 | Witten et al. | |
| 6,063,758 A | 5/2000 | Lappi et al. | |
| 6,203,803 B1 | 3/2001 | De Lacharriere et al. | |
| 6,221,846 B1 | 4/2001 | Nishida et al. | |
| 6,235,291 B1 | 5/2001 | De Lacharriere et al. | |
| 6,333,042 B1 | 12/2001 | De Lacharriere et al. | |
| 6,573,244 B1 | 6/2003 | Gordon et al. | |
| 6,596,692 B1 | 7/2003 | Burman et al. | |
| 6,673,603 B2 | 1/2004 | Baetge et al. | |
| 6,689,165 B2 | 2/2004 | Jacob et al. | |
| 6,709,651 B2 | 3/2004 | Grouzmann et al. | |
| 6,841,551 B2 | 1/2005 | Nimmo et al. | |
| 7,071,166 B2 * | 7/2006 | Nishida et al. .............. 514/8.5 |
| 2003/0165482 A1 | 9/2003 | Rolland et al. | |
| 2003/0170205 A1 | 9/2003 | Sheppard | |
| 2003/0181386 A1 | 9/2003 | Nishida et al. | |
| 2004/0208934 A1 | 10/2004 | Royer | |
| 2004/0253248 A1 | 12/2004 | Lappi et al. | |
| 2005/0113304 A1 | 5/2005 | Gordon et al. | |

FOREIGN PATENT DOCUMENTS

| | | |
|---|---|---|
| WO | WO 01/02021 A2 | 1/2001 |
| WO | WO 2004/019865 A3 | 3/2004 |
| WO | WO 2004/058155 A2 | 7/2004 |
| WO | WO 2004/091649 A1 | 10/2004 |
| WO | WO 2005/014105 A1 | 2/2005 |

OTHER PUBLICATIONS

Vloemans et al.; "A newly developed hydrofibre dressing, in the treatment of partial-thickness burns"; *Burns* 27(2):167-173 (2001).
Siepmann et al.; "Mathematical modeling of bioerodible, polymeric drug delivery systems"; *Advanced Drug Delivery Reviews* 48:229-247 (2001).

\* cited by examiner

*Primary Examiner* — Robert Landsman
(74) *Attorney, Agent, or Firm* — Naomi S. Biswas; Patent GC

(57) ABSTRACT

Healing of wounds in mammalian tissue may be enhanced by the application of certain neuropeptides, optionally in combination with known growth promoting hormones. Exemplary neuropeptides include tachykinins, such as Substance P, Substance K, and the like, as well as calcitonin gene-related peptides. The compositions may further include a polymeric delivery carrier and are utilized by applying to the site of the wound. Wounds may be vascular or avascular wounds. The compositions promote elaboration of cellular matrices and development of cellular attachment mechanisms in addition to stimulating cellular proliferation.

3 Claims, 15 Drawing Sheets

FIGURE 1

| Treatment group | Wound Size* Day 0 | Wound Size Day 6 | Decrease % |
|---|---|---|---|
| Control | 47.9 ± 6.1 ** (42.0 – 59.5) | 33.3 ± 6.5 (29.3 – 45.5) | 30.4 ± 11.6 (7.1 – 50.0) |
| Substance P | 48.4 ± 8.5 (35.0 – 63.9) | 28.3 ± 7.3 (15.0 – 39.0) | 41.6 ± 15.0 (14.9 – 66.7) |
| Selenocystamine | 44.6 ± 7.3 (30.0 – 56.0) | 30.4 ± 8.2 (18.0 – 56.0) | 31.8 ± 18.3 (-2.9 – 52.5) |

\* mean values for wounds on day one had no statistically significant differences \*\* values are mean ± SE of estimated wound area and range of estimated wound area (sagittal x transverse)

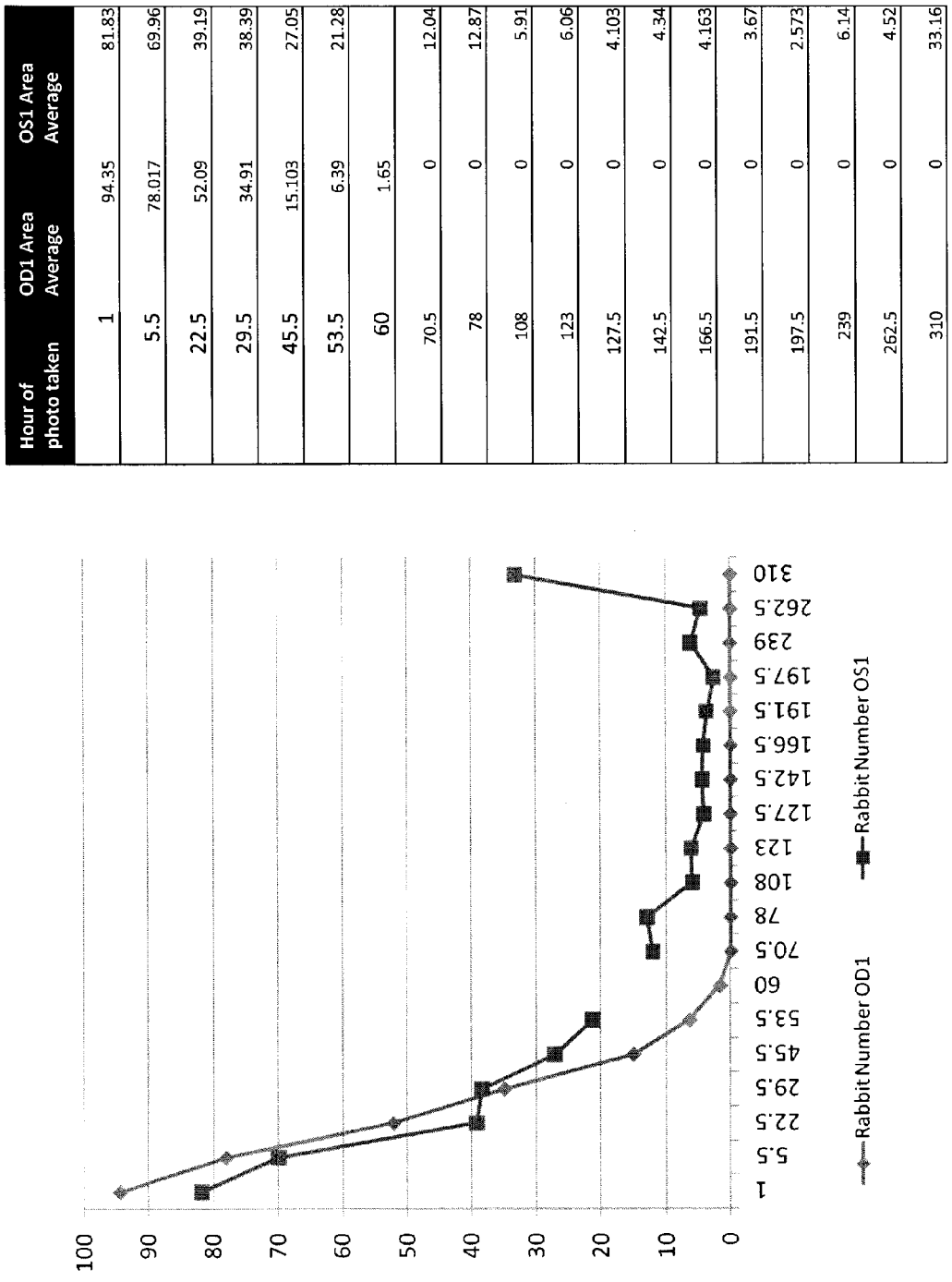
Figure 3: Rabbit No. 1

Figure 3 (Continued): Rabbit No. 2
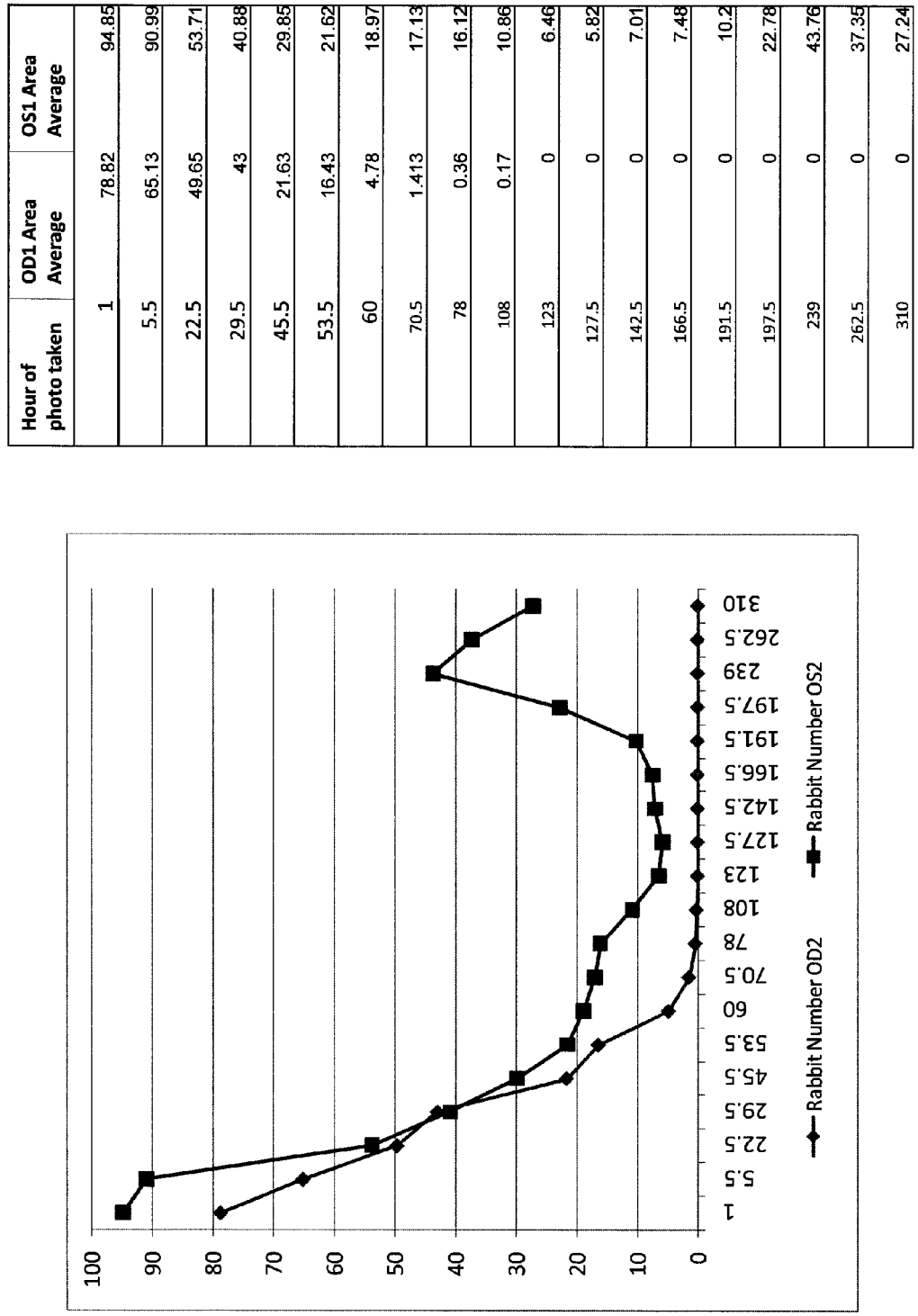
| Hour of photo taken | OD1 Area Average | OS1 Area Average |
|---|---|---|
| 1 | 78.82 | 94.85 |
| 5.5 | 65.13 | 90.99 |
| 22.5 | 49.65 | 53.71 |
| 29.5 | 43 | 40.88 |
| 45.5 | 21.63 | 29.85 |
| 53.5 | 16.43 | 21.62 |
| 60 | 4.78 | 18.97 |
| 70.5 | 1.413 | 17.13 |
| 78 | 0.36 | 16.12 |
| 108 | 0.17 | 10.86 |
| 123 | 0 | 6.46 |
| 127.5 | 0 | 5.82 |
| 142.5 | 0 | 7.01 |
| 166.5 | 0 | 7.48 |
| 191.5 | 0 | 10.2 |
| 197.5 | 0 | 22.78 |
| 239 | 0 | 43.76 |
| 262.5 | 0 | 37.35 |
| 310 | 0 | 27.24 |

Figure 3 (Continued): Rabbit No. 3
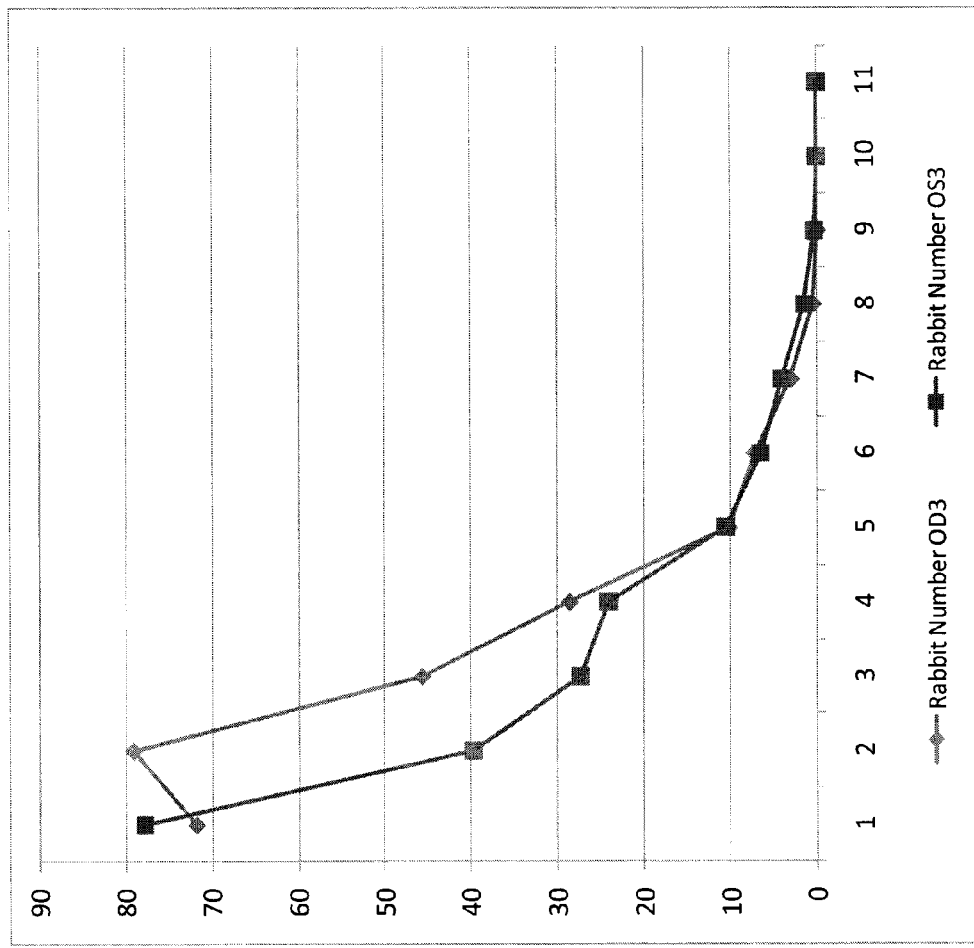
| OD3 Area Average | OS3 Area Average |
|---|---|
| 71.84 | 77.88 |
| 79.22 | 39.73 |
| 45.71 | 27.31 |
| 28.67 | 24.04 |
| 10.2 | 10.51 |
| 7.163 | 6.48 |
| 3.02 | 3.99 |
| 0.41 | 1.42 |
| 0 | 0.23 |
| 0 | 0 |
| 0 | 0 |

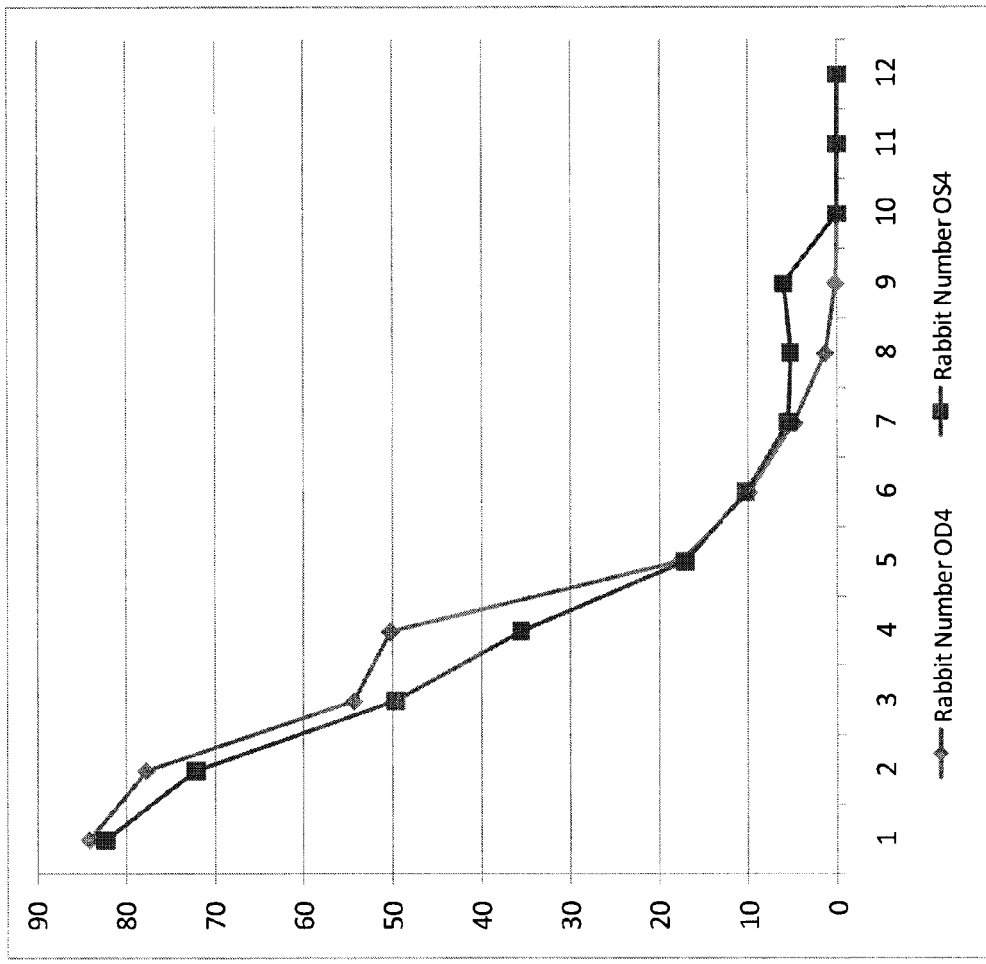
Figure 3 (Continued): Rabbit No. 4

Figure 3 (Continued): Rabbit No. 5
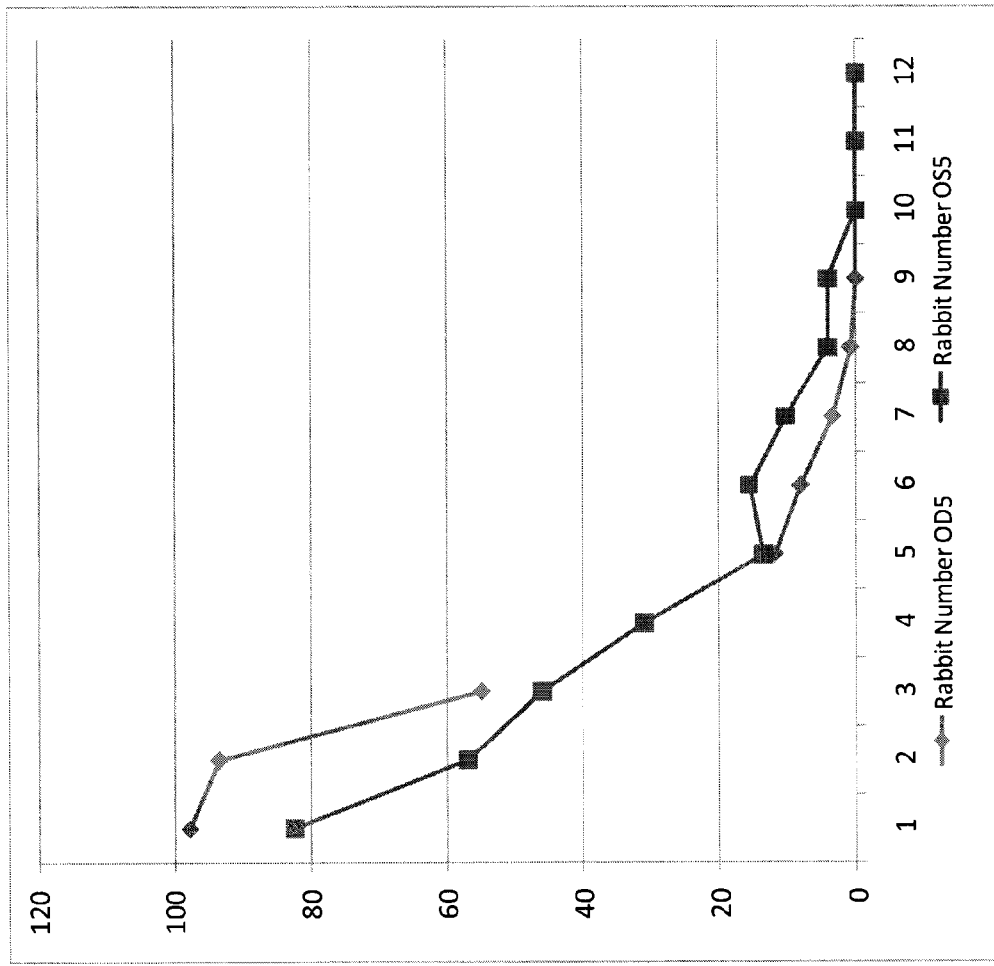

Figure 3 (Continued): Rabbit No. 6
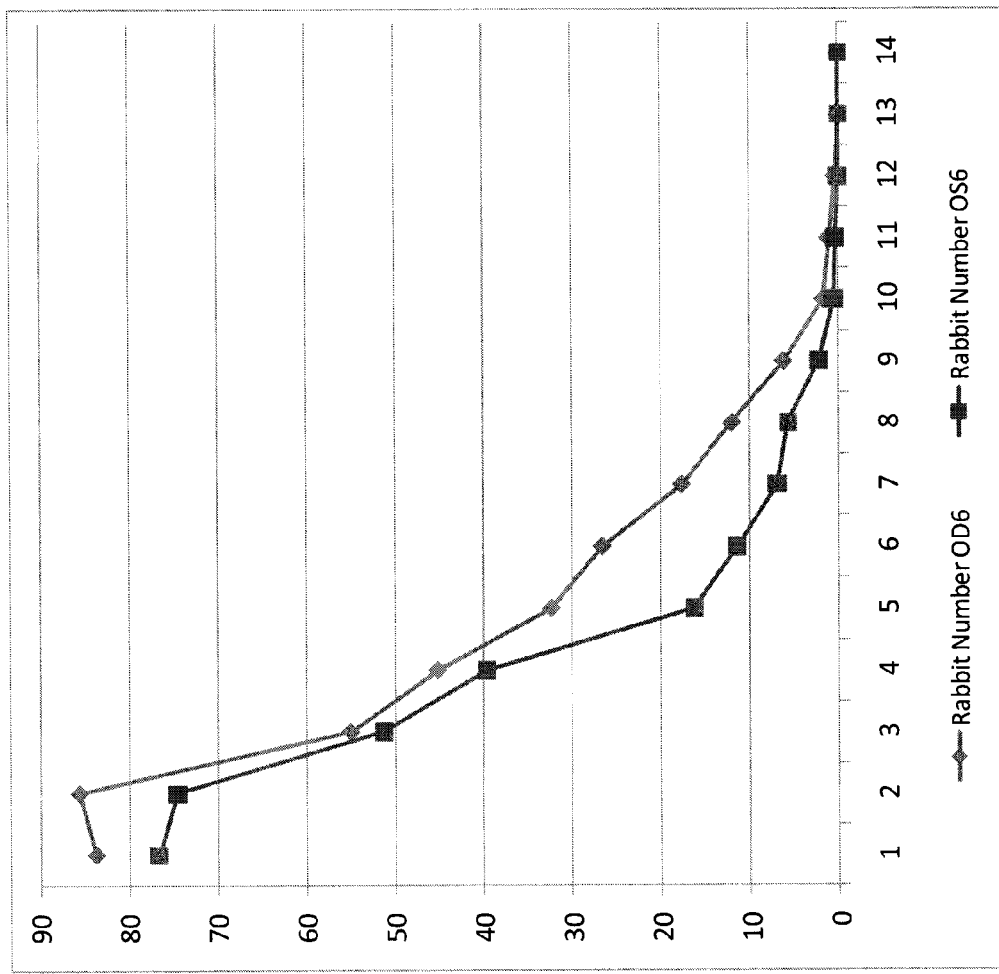

FIGURE 5

| SEQ ID NO: | Shorthand Designation | Structure (Molecular Formula for the M+1 Ion) | Calcd Mass (M+1) | Obsd Mass[a] (M+1) |
|---|---|---|---|---|
| 11 | 7S-(βMeF)SP | R-P-K-P-Q-Q-[SβMeF]-F-G-L-M-NH$_2$ (C$_{64}$H$_{101}$N$_{18}$O$_{13}$S) | 1361.7516 | 1361.7459 |
| 12 | 7R-(βMeF)SP | R-P-K-P-Q-Q-[RβMeF]-F-G-L-M-NH$_2$ (C$_{64}$H$_{101}$N$_{18}$O$_{13}$S) | 1361.7516 | 1361.7474 |
| 13 | 8S-(βMeF)SP | R-P-K-P-Q-Q-F-[SβMeF]-G-L-M-NH$_2$ (C$_{64}$H$_{101}$N$_{18}$O$_{13}$S) | 1361.7516 | 1361.7456 |
| 14 | 8R-(βMeF)SP | R-P-K-P-Q-Q-F-[RβMeF]-G-L-M-NH$_2$ (C$_{64}$H$_{101}$N$_{18}$O$_{13}$S) | 1361.7516 | 1361.7478 |
| 15 | 7S,8S-(βMeF)$_2$SP | R-P-K-P-Q-Q-[SβMeF]-[SβMeF]-G-L-M-NH$_2$ (C$_{65}$H$_{103}$N$_{18}$O$_{13}$S) | 1375.7672 | 1375.7669 |
| 16 | 7R,8S-(βMeF)$_2$SP | R-P-K-P-Q-Q-[RβMeF]-[SβMeF]-G-L-M-NH$_2$ (C$_{65}$H$_{103}$N$_{18}$O$_{13}$S) | 1375.7672 | 1375.7625 |
| 17 | 7R,8R-(βMeF)$_2$SP | R-P-K-P-Q-Q-[RβMeF]-[RβMeF]-G-L-M-NH$_2$ (C$_{65}$H$_{103}$N$_{18}$O$_{13}$S) | 1375.7672 | 1375.7617 |
| 18 | 7S,8R-(βMeF)$_2$SP | R-P-K-P-Q-Q-[SβMeF]-[RβMeF]-G-L-M-NH$_2$ (C$_{65}$H$_{103}$N$_{18}$O$_{13}$S) | 1375.7672 | 1375.7637 |

[a] From the fast atom bombardment mass spectrum.

FIGURE 7

| Structure | 5,6-Q-α | 5,6-Q-β | 7-F-α | 7-F-β | 8-F-α | 8-F-β | 9-G |  |
|---|---|---|---|---|---|---|---|---|
| SP | 4.15 | 1.85-2.10 | 4.48 | 2.91 | | 4.50 | 3.19 | 3.93, 3.83 |
| 8R-(βMeF)SP | 4.39 | 2.48-2.60 | 4.56 | 3.1, 2.95 | | 4.53 | 3.33 | 3.81, 3.755 |
| 8S-(β MF)SP | 4.49 | 2.45-2.60 | 4.32 | 2.85, 2.57 | | 4.49 | 3.25 | 3.92, 3.875 |
| 7R-(β MF)SP | 4.20, 4.41 | 2.10-2.15 | 4.39 | 3.19 | | 4.40 | 2.84, 3.18 | 3.83, 3.705 |
| 7S-(β MF)SP | | | No Data Available | | | | | |

* A dash between the numbers indicates a signal shift range where overlapping signals made discrete assignments impossible. A comma indicates values for separate protons.

FIGURE 9

| Peptide | Rabbit Iris EC50 nM 37°C | Rabbit Iris Hill Coef | Rabbit Iris 25°C | Rat NK1 |
|---|---|---|---|---|
| 8R-(bMF)SP | 0.13 ±0.003 | 1.8±0.075 | | 5.3 |
| 7S8S-(bMF)2SP | 0.18 ±0.024 | 1.2±0.17 | | 7.8 |
| 7R8S-(bMF)2SP | 0.28 ±0.013 | 1.4±0.080 | | 35 |
| 7S-(bMF)SP | 0.54 ±0.016 | 1.5±0.056 | 1.1 | 40 |
| 7S8R-(bMF)2SP | 0.58 ±0.049 | 1.1±0.088 | | 7.7 |
| 7R-(bMF)SP | 0.59 ±0.024 | 1.4±0.071 | | 400 |
| SP | 0.61 ±0.031 | 1.1±0.055 | | 1.5 |
| 8S-(bMF)SP | 5.76 ±0.29 | 1.1±0.057 | 13.1 | 0.21 |
| 7R8R-(bMF)2SP | 10.0 ±0.43 | 1.8±0.13 | | 1200 |

SEQUENCE LISTING

<160> NUMBER OF SEQ ID NOS: 10

<210> SEQ ID NO 1
<211> LENGTH: 11
<212> TYPE: PRT

<213> ORGANISM: Homo sapiens

<400> SEQUENCE: 1

Arg Pro Lys Pro Gln Gln Phe Phe Gly Leu Met
1               5                   10

<210> SEQ ID NO 2
<211> LENGTH: 10
<212> TYPE: PRT
<213> ORGANISM: Homo sapiens

<400> SEQUENCE: 2

His Lys Ile Asp Ser Phe Val Gly Leu Met
1               5                   10

<210> SEQ ID NO 3
<211> LENGTH: 10
<212> TYPE: PRT
<213> ORGANISM: Homo sapiens

<400> SEQUENCE: 3

Asp Met His Asp Phe Phe Val Gly Leu Met
1               5                   10

<210> SEQ ID NO 4
<211> LENGTH: 11
<212> TYPE: PRT
<213> ORGANISM: Homo sapiens

<400> SEQUENCE: 4

Glu Ala Asp Pro Asn Lys Phe Tyr Gly Leu Met
1               5                   10

<210> SEQ ID NO 5
<211> LENGTH: 11
<212> TYPE: PRT
<213> ORGANISM: Homo sapiens

<400> SEQUENCE: 5

Glu Pro Ser Lys Asp Ala Phe Ile Gly Leu Met
1               5                   10

<210> SEQ ID NO 6
<211> LENGTH: 12
<212> TYPE: PRT
<213> ORGANISM: Homo sapiens

<400> SEQUENCE: 6

Asp Val Pro Lys Ser Asp Gln Phe Val Gly Leu Met
1               5                   10

<210> SEQ ID NO 7
<211> LENGTH: 37
<212> TYPE: PRT
<213> ORGANISM: Homo sapiens

<400> SEQUENCE: 7

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
            35

```
<210> SEQ ID NO 8
<211> LENGTH: 6
<212> TYPE: PRT
<213> ORGANISM: Homo sapiens

<400> SEQUENCE: 8

Gln Phe Phe Gly Leu Met
1               5

<210> SEQ ID NO 9
<211> LENGTH: 11
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: Norleucine

<400> SEQUENCE: 9

Arg Pro Lys Pro Gln Gln Phe Phe Gly Leu Xaa
1               5                   10

<210> SEQ ID NO 10
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (7)..(7)
<223> OTHER INFORMATION: D-Trp
<220> FEATURE:
<221> NAME/KEY: MISC_FEATURE
<222> LOCATION: (9)..(9)
<223> OTHER INFORMATION: D-Trp
<220> FEATURE:
<221> NAME/KEY: MISC_FEATURE
<222> LOCATION: (11)..(11)
<223> OTHER INFORMATION: D-Trp

<400> SEQUENCE: 10

Xaa Pro Lys Pro Gln Gln Xaa Phe Gly Leu Leu
1               5                   10
```

… # METHODS OF USING SUBSTANCE P TO PROMOTE HEALING OF VASCULAR WOUNDS

CROSS REFERENCE TO RELATED APPLICATIONS

The present application is a continuation of U.S. Ser. No. 11/603,541, filed Nov. 21, 2006, now abandoned; which claims benefit under 35 U.S.C. 119(e) of provisional applications U.S. Ser. No. 60/738,910, filed Nov. 22, 2005; U.S. Ser. No. 60/739,154, filed Nov. 22, 2005; and U.S. Ser. No. 60/740,489, filed Nov. 28, 2005. The entire contents of each of the above-referenced patents and patent applications are hereby expressly incorporated herein by reference.

STATEMENT REGARDING FEDERALLY SPONSORED RESEARCH AND DEVELOPMENT

Not applicable.

BACKGROUND OF THE INVENTION

1. Field of the Invention

The present invention relates generally to methods and compositions for the enhancement of cellular proliferation and for the treatment of wounds and other disorders. More specifically, the invention relates to the use of neuropeptides for wound treatment in general and corneal wound treatment and vascular wound treatment in particular and, more particularly, to the use of Substance P and analogs and conjugates thereof for such wound treatment, wherein the neuropeptide is incorporated into a delivery vehicle that contains a polymeric delivery carrier that increases the dwell time of the neuropeptide, thereby reducing the number of administrations required when compared to administration of the neuropeptide alone.

2. Detailed Description of the Background Art

Traumatic injury and disease can cause damage to the skin, tissue, and body organs that requires cellular regeneration for healing. Accidental injuries such as cuts, abrasions, burns, and intentional surgical procedures result in wounds that can affect large areas of the skin or affected body organs and can require lengthy periods to heal. Long healing times are a particular problem with denervated regions of the extremities and with wounds on sensitive areas, such as corneal wounds and wounds on the bottom of the feet, buttocks and other weight bearing surfaces, which are difficult to treat over prolonged periods. For these reasons, it would be desirable to provide methods and pharmacological agents which can be used to promote rapid healing of wounds and other injuries to the skin, tissue, and body organs.

A variety of cellular growth promoting hormones have been identified that are capable of enhancing cellular proliferation, and these hormones have been used in the treatment of wounds. Exemplary growth promoting hormones include, but are not limited to, cytokines, lymphokines, interleukins, chemokines, epidermal growth factor, platelet-derived growth factor, insulin, insulin-like growth factor, transforming growth factor-β, nerve cell growth factor, fibroblast growth factor, platelet-derived growth factor, granulocyte-colony stimulating factor, granulocyte-macrophage colony stimulating factor, neurotropins, erythropoietin, thrombopoietin, myostatin, growth differentiating factor-9, hepatocyte growth factor, and the like. While use of these hormones continues to hold promise, no one growth promoting agent is known to be optimal for all situations. Thus, it would be desirable to identify additional substances and compositions which have therapeutic value as growth promoting agents, and it would be further desirable to identify substances and compositions which are capable of enhancing or modulating the effect of these and other growth promoting substances alone or in combination with other substances.

In addition to cellular proliferation, wound healing requires the elaboration of extracellular matrices and development of cellular attachment mechanisms in order to achieve normal tissue morphology. For example, the formation of fibronectin is an important function in normal wound healing. Without sufficient expression of fibronectin and other cellular matrix substances, regenerated tissue can have an abnormal morphology. Thus, it would be desirable to identify substances and compositions which could promote such additional wound healing responses.

U.S. Pat. No. 5,616,562, issued to Murphy et al. on Apr. 1, 1997 and expressly incorporated herein by reference in its entirety, discloses methods and compositions using Substance P to promote wound healing. The '562 patent discloses methods of healing a corneal or epithelial wound in a Substance P deficient patient, and such methods require multiple administrations of Substance P at frequent time intervals to treat the corneal or epithelial wound. Therefore, methods of treating corneal or epithelial wounds with a composition including Substance P that could increase the dwell time of the Substance P and thereby decrease the required number of administrations of the composition, are desired. In addition, methods of treating wounds other than corneal or epithelial wounds with Substance P are also desired.

For the above reasons, it is an object of the present invention to provide pharmacological agents and formulations useful for the topical treatment of wounds and other disorders. Desirably, the compositions will be capable of providing a potent mitogenic activity which enhances the proliferation of epithelial cells, fibroblasts, and the like. The compositions, in certain embodiments, should also be capable of stimulating the expression of extracellular matrices and development of cellular attachment mechanisms which contribute to normal morphology in the healed tissue. In one embodiment, the compositions should be capable of enhancing or modulating the growth promoting activity of other growth promotants. The compositions should be suitable for topical application to the skin and body organs, including the eye and skin, and should also be suitable for administration to treat vascular wounds. In addition, the compositions of the present invention should further be suitable for incorporation into a wide variety of delivery vehicles such as but not limited to, salves, lotions, creams which may or may not include such additional components as Aloe Vera, Oat Beta Glucan, Hyaluronic Acid and other large polymeric delivery carriers.

SUMMARY OF THE INVENTION

According to the present invention, neuropeptides, including but not limited to, tachykinins, calcitonin gene-related peptide, analogs thereof, and conjugates thereof are applied topically to wounds in mammalian tissue in order to promote healing. Such neuropeptides have been found to possess cellular growth promoting activity when administered alone to a wound in tissue and have been further found to provide enhanced growth promoting activity when combined with other cellular growth promotants, such as epidermal growth factor, transforming growth factor-β, insulin, insulin-like growth factor, nerve growth factor, and platelet derived growth factor. In addition, the neuropeptides have been found to promote the elaboration of cellular matrices and the development of cellular attachment mechanisms which enhance the regeneration of tissue having a substantially normal morphology.

Compositions according to the present invention include the neuropeptide and/or an analog and/or a conjugate thereof present in a vehicle suitable for topical application and may optionally include a growth promoting hormone, such as one of the growth promotants listed herein. According to one method of the present invention, the compositions are applied in an amount and at a concentration sufficient to promote healing of the wound being treated. Wounds which may be treated include cutaneous wounds, corneal wounds, wounds to the epithelial-lined hollow body organs, vascular wounds, and the like. Such wounds may result from trauma, surgical procedures, and disease.

The compositions of the present invention also include Substance P present in a vehicle suitable for topical application in mammalian tissues, in particular, for ocular or cutaneous application. The preferred Substance P compositions of the method of the present invention may be applied to a patient in an amount and at a concentration sufficient to promote healing of the wound being treated. Any wound may be treated advantageously with Substance P; examples of wounds that may be treated by Substance P include, but are not limited to, epithelial and corneal wounds, cutaneous non-healing wounds, or wounds that result from any one or more of the following conditions of metaherpetic keratitis, viral infection, galactosemic or diabetic keratopathy, thermal or chemical burns, nerve destruction, corneal epithelial defect and failure to heal post penetrating keratoplasty.

The present invention includes methods for promoting healing of a wound in a patient, wherein the methods include applying a composition to the wound in an amount sufficient to promote healing of the wound. The compositions utilized in such method comprise substance P or at least one analog thereof and a polymeric delivery vehicle, wherein the polymeric delivery vehicle present in the composition increases the dwell time of the substance P or at least one analog thereof such that the number of administrations of the composition required for promoting healing of the wound in the patient is reduced when compared to the number of administrations required for substance P or at least one analog thereof alone. The polymeric delivery vehicle may be selected from the group consisting of hyaluronic acid, chondroitin, hydroxymethyl cellulose, paraffin, cetyl alcohol, polyethylene glycol, gelatin, sodium alginate, methyl cellulose, carboxymethyl cellulose, plastibase hydrophilic gelatin, dextrin, stearyl alcohol, polyethylene glycol, polyvinyl alcohol, methoxyethylene-maleic anhydride, nanoparticles, liposomes, combinations thereof, modifications thereof and derivatives thereof.

The compositions utilized in such methods may further include at least one growth factor, which may be selected from the group consisting of cytokines, lymphokines, interleukins, chemokines, epidermal growth factor, platelet-derived growth factor, insulin, insulin-like growth factor, transforming growth factor-β, nerve cell growth factor, fibroblast growth factor, platelet-derived growth factor, granulocyte-colony stimulating factor, granulocyte-macrophage colony stimulating factor, neurotropins, erythropoietin, thrombopoietin, myostatin, growth differentiating factor-9, hepatocyte growth factor, and combinations thereof.

The wound to which the composition is applied may be a vascular wound, such as but not limited to, burns, diabetic ulcers, decubitus ulcers, and venous stasis ulcers.

The present invention further includes compositions that comprise Substance P or at least one analog thereof and a polymeric delivery vehicle, wherein the substance P or at least one analog thereof and the polymeric delivery vehicle are present in a lotion, cream or ointment suitable for cutaneous application. The polymeric delivery vehicle may be selected from the group consisting of hyaluronic acid, chondroitin, hydroxymethyl cellulose, paraffin, cetyl alcohol, polyethylene glycol, gelatin, sodium alginate, methyl cellulose, carboxymethyl cellulose, plastibase hydrophilic gelatin, dextrin, stearyl alcohol, polyethylene glycol, polyvinyl alcohol, methoxyethylene-maleic anhydride, nanoparticles, liposomes, combinations thereof, modifications thereof and derivatives thereof. The composition may further include at least one growth factor that may be selected from the group consisting of cytokines, lymphokines, interleukins, chemokines, epidermal growth factor, platelet-derived growth factor, insulin, insulin-like growth factor, transforming growth factor-β, nerve cell growth factor, fibroblast growth factor, platelet-derived growth factor, granulocyte-colony stimulating factor, granulocyte-macrophage colony stimulating factor, neurotropins, erythropoietin, thrombopoietin, myostatin, growth differentiating factor-9, hepatocyte growth factor, and combinations thereof.

The present invention is also directed to wound dressings that include a natural or synthetic bandage having a composition embedded or impregnated therein or coated thereon, wherein the composition comprises Substance P or at least one analog thereof and a polymeric delivery vehicle. The polymeric delivery vehicle of the composition may be selected from the group consisting of hyaluronic acid, chondroitin, hydroxymethyl cellulose, paraffin, cetyl alcohol, polyethylene glycol, gelatin, sodium alginate, methyl cellulose, carboxymethyl cellulose, plastibase hydrophilic gelatin, dextrin, stearyl alcohol, polyethylene glycol, polyvinyl alcohol, methoxyethylene-maleic anhydride, nanoparticles, liposomes, combinations thereof, modifications thereof and derivatives thereof. The composition of the wound dressing may further include at least one growth factor that may be selected from the group consisting of cytokines, lymphokines, interleukins, chemokines, epidermal growth factor, platelet-derived growth factor, insulin, insulin-like growth factor, transforming growth factor-β, nerve cell growth factor, fibroblast growth factor, platelet-derived growth factor, granulocyte-colony stimulating factor, granulocyte-macrophage colony stimulating factor, neurotropins, erythropoietin, thrombopoietin, myostatin, growth differentiating factor-9, hepatocyte growth factor, and combinations thereof.

The present invention further includes methods for promoting healing of a vascular wound in a patient. Such methods include applying a composition to the vascular wound in an amount sufficient to promote healing of the vascular wound, wherein the composition comprises substance P or at least one analog thereof. The composition may further include at least one growth factor that may be selected from the group consisting of cytokines, lymphokines, interleukins, chemokines, epidermal growth factor, platelet-derived growth factor, insulin, insulin-like growth factor, transforming growth factor-β, nerve cell growth factor, fibroblast growth factor, platelet-derived growth factor, granulocyte-colony stimulating factor, granulocyte-macrophage colony stimulating factor, neurotropins, erythropoietin, thrombopoietin, myostatin, growth differentiating factor-9, hepatocyte growth factor, and combinations thereof.

Other objects, features and advantages of the present invention will become apparent from the following detailed description when read in conjunction with the accompanying figures and appended claims.

BRIEF DESCRIPTION OF THE DRAWINGS

FIG. 1 represents data comparing wound areas (size in square millimeter) and percentage decrease in wound areas for punch wounds in rats treated with substance P or selenocystamine.

FIG. 3 illustrates the average healing time in 6 rabbits with persistent epithelial defects after treatment with Substance P and IGF-1 in an HA vehicle, versus control. Wound area is provided here in square millimeter.

FIG. 5 is a chart containing the structure, shorthand designation, SEQ ID NO:, and calculated and observed masses for the β-Methylphenylalanine-Containing Substance P analogs.

FIG. 7 represents the selected $^1$H NMR data for SP analogs with $CD_3OH$. NMR shifts are in ppm.

FIG. 9 illustrates the biological activity of the βMeF-containing SP analogs.

DESCRIPTION OF THE PREFERRED EMBODIMENTS

Figure 2:
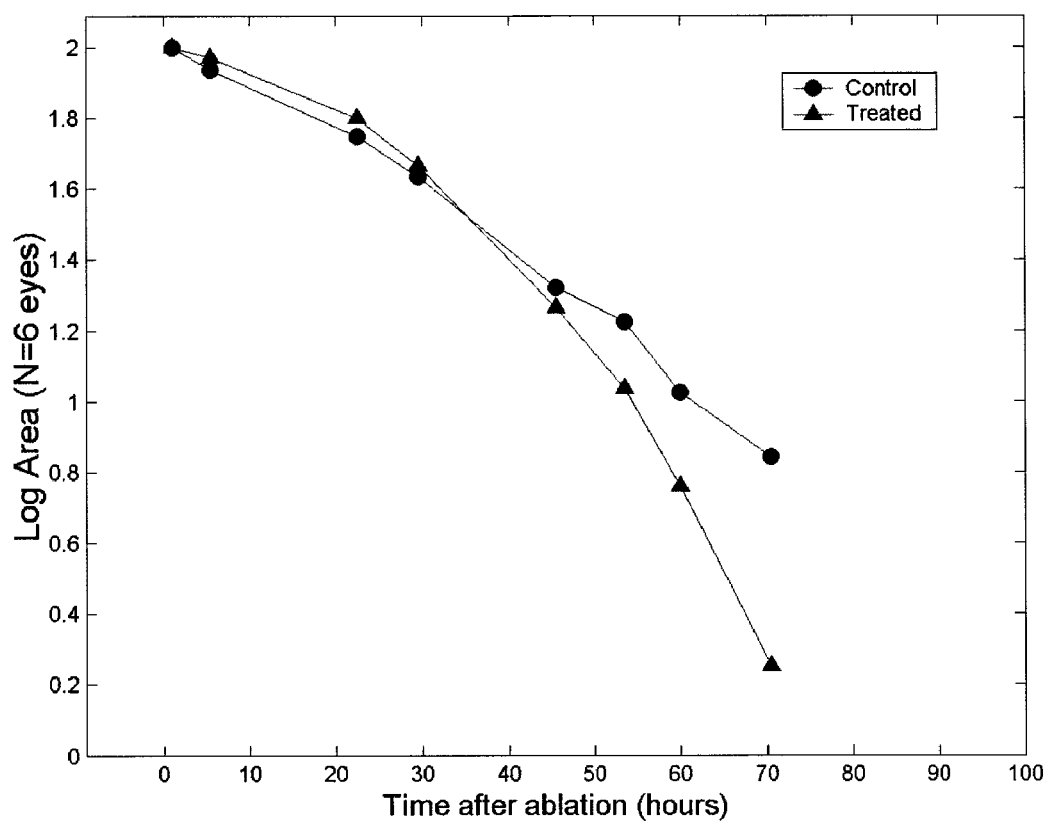
FIG. 2 illustrates an analysis of the rate of epithelial healing after photorefractive keratectomy (PRK) in rabbits after treatment with Substance P and IGF-1 in an HA vehicle, versus control. Wound area is provided here in square centimeter.
Figure 4:
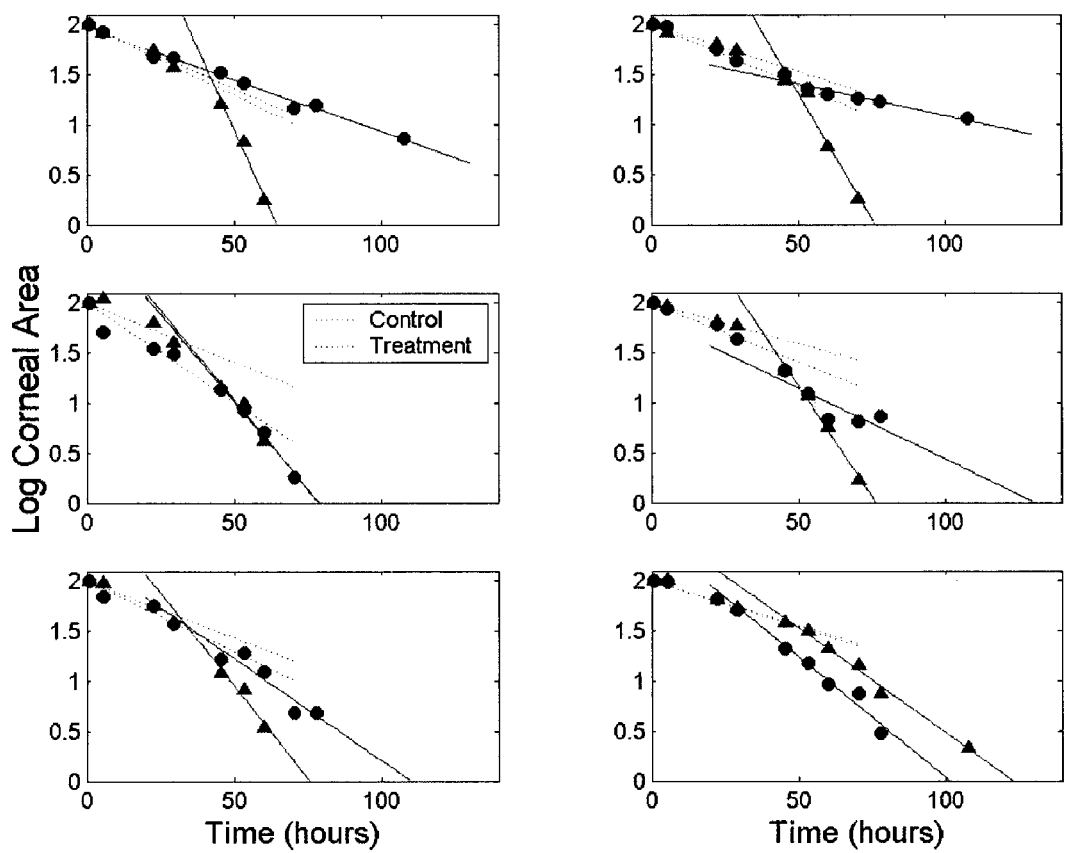
FIG. 4 illustrates a two component model of corneal healing rates. Wound area is provided here in square centimeter.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein are for the purposes of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

In as much as additional references, articles, journals and the like are mentioned or cited herein, each such item is expressly incorporated herein by reference in its entirety as if it were set forth herein explicitly. Initially, U.S. Pat. No. 5,616,562 is expressly incorporated herein by reference in its entirety.

Substance P ("SP") and Substance K ("SK") have been found to provide enhanced proliferation in cell cultures of smooth muscle cells and human skin fibroblasts. Substance P enhances proliferation of human T-lymphocytes, and such enhancement is mediated by specific receptors for Substance P. Substance P has also been found to stimulate the release of prostaglandin $E_2$ ($PGE_2$) from and enhance the proliferation of rheumatoid synoviocytes. Substance P has been identified in developing ocular tissue by immunofluorescence. Systemic capsaicin treatment blocks the activity of Substance P in animal models and can cause corneal ulcers.

Diabetes has adverse effects on many tissues including the cornea. Diabetic patients have been shown to have a very high frequency (approx. 50%) of corneal epithelial abnormalities. It has been suggested that the corneal epithelia of diabetic animals has an increased rate of exfoliation, and the basement membranes of the eye are thickened in diabetic humans and animals. Corneal endothelial morphology is also altered in prolonged diabetic states in man and dogs. During the course of prolonged retinal surgeries to treat proliferative vitreoretinopathy (a commonly encountered vision threatening consequence of long standing diabetes), the corneal epithelium must occasionally be removed to allow better visualization of the posterior segment. Normal patients typically have no difficulties in re-epithelializing the corneal surface, while diabetic patients frequently have delayed healing. Impaired corneal epithelial wound healing has also been documented in diabetic rats and in galactosemic rats.

The effect of diabetes on SP content varies with the structure being investigated. Deficits in anterograde and retrograde transport of SP have been documented in the nerves of diabetic rats. Significant reduction of SP-like immunoreactivity was shown in the spinal cord, sciatic nerve, autonomic nerves, and many peripheral nerves of diabetic rats.

Neuropeptides preferred for use in the present invention include those which possess binding specificity for mammalian cell receptor(s) that are capable of promoting cellular proliferation as well as the elaboration of cellular matrices, such as fibronectin, and the development of cellular attachment mechanisms. Exemplary naturally-occurring neuropeptides include tachykinins such as Substance P, Substance K (neurokinen A), neurokinen B, physalaemin, eledoisin, and kassinin; calcitonin gene-related peptide; and other sensory nerve neuropeptides; with the use of Substance P and its analogs and conjugates being preferred. For the most part, tachykinins are localized in sensory nerve endings, although not in all cases. Calcitonin gene-related peptide is a sensory nerve neuropeptide, and the present invention may employ sensory nerve neuropeptides in addition to or in composition with those which are listed above. In addition to naturally-occurring neuropeptides, the compositions of the present invention can utilize synthetic neuropeptides, neuropeptide analogs, neuropeptide fragments, as well as agonists and other substances capable of specifically binding to the neuropeptide receptor(s) of interest.

Substance P is an undecapeptide having an amino acid sequence of RPKPQQFFGLM (SEQ ID NO:1). Substance K is a decapeptide having an amino acid sequence of HKIDSFVGLM (SEQ ID NO:2). Neurokinen B is a decapeptide having an amino acid sequence of DMHDFFVGLM (SEQ ID NO:3). Physalaemin is an undecapeptide having an amino acid sequence of EADPNKFYGLM (SEQ ID NO:4). Eledoisin is an undecapeptide having an amino acid sequence of EPSKDAFIGLM (SEQ ID NO:5). Kassinin is a dodecapeptide having an amino acid sequence of DVPKSDQFVGLM (SEQ ID NO:6). Calcitonin gene-related peptide is a 37 amino acid peptide having an amino acid sequence of SCNTATCVTHRLAGLLSRSGGVVKDNFVPTNVGSEAF (SEQ ID NO:7).

The amino acid sequences of these neuropeptides need not correspond precisely to the above amino acid sequences, but rather may include only a portion of such sequences. Usually, the peptides will include at least six of the amino acids, and may include at least nine of the amino acids, and may further include amino acids in addition to those set forth in the above sequences located at either the N-terminus or C-terminus. When additional amino acids are incorporated, the resulting peptide compositions will usually contain 100 or fewer amino acids in total, usually containing fifty or fewer amino acids in total, and more usually containing twenty-five or fewer amino acids in total (in the case of tachykinin derivatives). The neuropeptide compositions of the present invention may also embody substitutions of particular amino acids, although there will usually be no more than three substitutions in peptides containing ten or fewer amino acids in total. Such substitutions, of course, should not substantially diminish the desired growth promoting activity of the neuropeptides, and in some cases may in fact enhance the desired activity or may contribute to another desired characteristic, such as longevity (resistance to degradation), persistence, or the like.

A particular fragment of Substance P including only amino acids 6-11 (QFFGLM (SEQ ID NO:8) has been found to be active in promoting cellular growth and may, in at least some applications, display enhanced activity relative to intact Substance P.

A particular substitution peptide where norleucine has been substituted for the C-terminus methionine in Substance P (SEQ ID NO:9) has been found to display enhanced activity under at least some treatment conditions, as described in greater detail in the Experimental section hereinafter.

In some cases, it may be desirable to incorporate one or more non-natural amino acids in the synthetic neuropeptides of the present invention. Possible non-natural amino acids will usually have at least an N-terminus and a C-terminus and will have side chains that are either identical to or chemically modified or substituted from a natural amino acid counterpart. An example of a non-natural amino acid is an optical isomer of a naturally-occurring L-amino acid. A particular analog of Substance P incorporating non-natural amino acids which has been found to stimulate epithelial cell growth is spantide which has the same sequence as Substance P except that a D-Arg is substituted for Arg at position 1, D-Trp is substituted for Phe and Gly at positions 7 and 9, respectively, and Leu is substituted for Met at position 11 (SEQ ID NO:10). Other examples of chemical modifications or substitutions include hydroxylation or fluorination of C—H bonds within natural amino acids.

In other embodiments, the present invention includes β-methylphenylalanine containing Substance P analogs, as described in greater detail herein after.

Such peptide modification techniques are used in the manufacture of drug analogs of biological compounds and are known to one of ordinary skill in the art and should be considered an integrated portion of the present disclosure.

Synthetic peptides having biological and binding activity the same as or similar to that of the natural neuropeptides may be produced by either of two general approaches. First, the polypeptides may be produced by the well-known Merrifield solid-phase chemical synthesis method wherein amino acids are sequentially added to a growing chain. Systems for manually synthesizing peptides on polyethylene pegs are available from Cambridge Research Biochemicals, Cambridge, Mass. Automatic peptide synthesis equipment is available from several commercial suppliers, including Applied Biosystems, Inc., Foster City, Calif.; Beckman Instruments, Inc., Waldwick, N.J.; and Biosearch, Inc., San Raphael, Calif. Using such automatic synthesizers according to manufacturer's instructions, peptides may be produced in gram quantities for use in the present invention.

Second, the synthetic neuropeptides of the present invention may be synthesized by recombinant techniques involving the expression in cultured cells of recombinant DNA molecules encoding a gene for a desired portion of a natural or analog molecule. The gene encoding the neuropeptide may itself be natural or synthetic. Conveniently, polynucleotides may be synthesized by well known techniques based on the desired amino acid sequence. For example, short single-stranded DNA fragments may be prepared by the phosphoramidite method. A double-stranded fragment may then be obtained either by synthesizing the complementary strand and annealing the strands together under appropriate conditions or by adding the complementary strand using DNA polymerase under appropriate conditions or by adding the complementary strand using DNA polymerase with an appropriate primer sequence. The natural or synthetic DNA fragments coding for the desired neuropeptide may then be incorporated in a suitable DNA construct capable of introduction to and expression in an in vitro cell culture. A particular technique for the recombinant DNA production of Substance P is described in Yokota et al. (1989) J. Biol. Chem. 264: 17649, the entire disclosure of which is explicitly incorporated herein by reference in its entirety.

The methods and compositions of the present invention may also employ synthetic non-peptide compositions that have biological activity functionally comparable to that of the known neuropeptides. By functionally comparable, it is meant that the shape, size, flexibility, stereochemistry and electronic configuration of the non-peptide molecule are such that the biological activity of the molecule is similar to or better than the neuropeptides. In particular, the non-peptide molecules should display comparable mitogenic activity and possess the ability to bind to the particular receptor(s) responsible for the wound healing activity provided by the neuropeptides, preferably including the ability to promote the elaboration of cellular matrices and the development of cellular attachment mechanisms. Such non-peptide molecules will typically be small molecules having a molecular weight in the range from about 100 to 1000 daltons. The use of such small molecules is frequently advantageous in the preparation of pharmacological compositions.

The identification of such nonpeptide analog molecules can be performed using techniques known in the art of drug design. Such techniques include, but are not limited to, self-consistent field (SCF) analysis, configuration interaction (CI) analysis, and normal mode dynamics computer analysis, all of which are well described in the scientific literature. Preparation of the identified compounds will depend on the desired characteristics of the compounds and will involve standard chemical synthetic techniques.

The compositions of the present invention comprise neuropeptides or their analogs incorporated in a physiologically-acceptable carrier suitable for topical application to the affected area. The compositions may contain from about 0.1 nM to 10 mM neuropeptide, usually containing from about 0.01 μM to 1 mM neuropeptide, and more usually containing from about 0.1 μM to 100 μM neuropeptide. The nature of the carrier will vary depending on the intended area of application. For application to the skin, a cream, a lotion, or ointment base is usually preferred, with suitable bases including lanolin, SILVADENE™ (Marion) (particularly for the treatment of burns), AQUAPHOR™ (Duke Laboratories, South Norwalk, Conn.), and the like.

The present invention also includes natural and synthetic bandages and other wound dressings that have been embedded, impregnated or coated with the compositions of the present invention to provide for continuous exposure of a wound to the neuropeptide. The present invention also includes aerosol applicators containing the compositions of the present invention. Further, the present invention also includes implantable devices, such as heart pacemakers, intralumenal stents, and the like, wherein the implantable devices have been coated with the compositions of the present invention, wherein the growth promoting activity of the compositions of the present invention would be of benefit in the environment of the implanted device. Coating may be achieved by non-specific adsorption or covalent attachment.

The compositions of the present invention may further comprise a polymeric delivery carrier that increases the dwell time of the neuropeptide, thereby reducing the number of administrations required when compared to administration of the neuropeptide alone. For example, the compositions of the present invention without the polymeric delivery carrier may require administration every fifteen minutes for two hours, while the compositions of the present invention including the polymeric delivery carrier may have similar effectiveness when administered in a single dose. The polymeric delivery carrier may be any compound that increases the dwell time of the neuropeptide and functions in accordance with the present invention as described herein. Examples of polymeric delivery carriers that may be utilized in accordance with the present invention include, but are not limited to, hyaluronic acid (HA), chondroitin, hydroxymethyl cellulose, paraffin, cetyl alcohol, polyethylene glycol, gelatin, sodium alginate, methyl cellulose, carboxymethyl cellulose, plastibase hydrophilic gelatin, dextrin, stearyl alcohol, polyethylene glycol, polyvinyl alcohol, methoxyethylene-maleic anhydride, nanoparticles, liposomes, combinations thereof, modifications thereof and derivatives thereof.

In a preferred embodiment, the polymeric delivery carrier is HA. Hyaluronic acid or "HA" is a linear polysaccharide of the glycosaminoglycan class and is composed of up to thousands of β(1,4)GlcUA-β(1,3)GlcNAc repeats. In vertebrates, HA is a major structural element of the extracellular matrix and plays roles in adhesion and recognition. HA has a high negative charge density and numerous hydroxyl groups, therefore, the molecule assumes an extended and hydrated conformation in solution. The viscoelastic properties of cartilage and synovial fluid are, in part, the result of the physical properties of the HA polysaccharide. HA also interacts with proteins such as CD44, RHAMM, and fibrinogen thereby influencing many natural processes such as angiogenesis, cancer, cell motility, wound healing, and cell adhesion.

Naturally produced HA may be commercially harvested from a variety of sources, such as but not limited to, rooster combs. Alternatively, HA may be harvested from recombinant cells expressing a recombinant HA synthase (HAS) gene or a mutant, modification or derivative thereof.

The various HA synthases ("HAS"), the enzymes that polymerize HA, utilize UDP-GlcUA and UDP-GlcNAc sugar nucleotide precursors in the presence of a divalent Mn, Mg, or Co ion to polymerize long chains of HA. The HA chains can be quite large ($n=10^2$ to $10^4$). In particular, the HASs are membrane proteins localized to the lipid bilayer at the cell surface. During HA biosynthesis, the HA polymer is transported across the bilayer into the extracellular space. In all HASs, a single species of polypeptide catalyzes the transfer of two distinct sugars. In contrast, the vast majority of other known glycosyltransferases transfer only one monosaccharide.

HasA (or spHAS) from Group A *Streptococcus pyogenes* was the first HA synthase to be described at the molecular level. The various vertebrate homologs (*Xenopus* DG42 or XlHAS1; murine and human HAS1, HAS2, and HAS3) and the viral enzyme, A98R, are quite similar at the amino acid level to certain regions of the HasA polypeptide chain (~30% identity overall) and were discovered only after the sequence of spHAS was disclosed in 1994.

The Class II HAS, pmHAS (from *Pasteurella multocida*), has many useful catalytic properties including the ability to elongate exogenous acceptors at the non-reducing end with HA chains. The homologous chondroitin synthase, pmCS, also is useful, but it adds chondroitin chains to the acceptor's non-reducing terminus.

The enzymes described herein above may be utilized to produce polymeric delivery carriers of the present invention that include polysaccharides or oligosaccharides of HA, chondroitin, and chimeric or hybrid molecules incorporating both HA and chondroitin. The polymeric delivery carriers of the present invention may also be produced by modified synthases that are controllable single-action catalysts that allow step-wise synthesis of polymers. An advantage of these mutant enzymes is that during synthesis of oligosaccharides, the intermediates do not need to be purified at every step, and each individual step can be driven to completion.

The polymeric delivery carriers of the present invention also include grafts of polysaccharide or oligosaccharide polymers, i.e. HA or chondroitin, produced using either a hyaluronan synthase or a chondroitin synthase or a heparin synthase. Modified versions of the HAS or CS or HS enzymes (whether genetically or chemically modified) can also be utilized to graft on polysaccharides of various size and composition, and such polysaccharides also fall within the scope of polymeric delivery carriers of the present invention. The polymeric delivery carriers of the present invention also include polysaccharides or oligosaccharides as described above attached to various substrates, as described in more detail in the applications incorporated by reference herein below.

Examples of methods of producing polysaccharides that may be utilized as polymeric delivery carriers in accordance with the present invention, as well as examples of recombinant enzymes that may utilized for the production thereof, are described in U.S. Pat. Nos. 6,444,447, issued Sep. 3, 2002; 6,455,304, issued Sep. 24, 2002; 6,833,264, issued Dec. 21, 2004; 6,852,514, issued Feb. 8, 2005; 6,855,502, issued Feb. 15, 2005; 6,951,743, issued Oct. 4, 2005; 6,987,023, issued Jan. 17, 2006; 6,991,921, issued Jan. 31, 2006; 7,019,011, issued Sep. 19, 2006; 7,026,159, issued Apr. 11, 2006; 7,029,880, issued Apr. 18, 2006; 7,060,466, issued Jun. 13, 2006; 7,060,469, issued Jun. 13, 2006; 7,087,413, issued Aug. 8, 2006; 7,091,008, issued Aug. 15, 2006; 7,094,581, issued Aug. 22, 2006; 7,115,405, issued Oct. 3, 2006; and RE37,336, issued Aug. 21, 2001; and Published US Application Nos. US2006/0116348 A1, published Jun. 11, 2006; US 2006/0183203 A1, published Aug. 17, 2006; US 2006/018896 A1, published Aug. 24, 2006; US 2003/0175902 A1, published Sep. 18, 2003; US 2004/0132143 A1, published Jul. 8, 2004; US 2006/0105431 A1, published May 18, 2006; US 2003/0099967 A1, published May 29, 2003; US 2004/0197868 A1, published Oct. 7, 2004; and US 2005/0164984 A1, published Jul. 28, 2005; the contents of each of which are hereby expressly incorporated herein by reference in their entirety. However, it is to be understood that the above list is not exhaustive, and that any recombinant enzyme capable of producing a polymeric delivery carrier capable of functioning in accordance with the present invention may be utilized herein.

One embodiment of the compositions of the present invention comprises neuropeptides or their analogs and a polymeric delivery vehicle incorporated in a physiologically-acceptable carrier suitable for topical application to the affected area. The compositions may contain from about 0.1 nM to 10 mM polymeric delivery carrier, such as from about 0.01 µM to 1 mM polymeric delivery carrier, or from about 0.1 µM to 100 µM polymeric delivery carrier.

For corneal treatment, the polymeric delivery carrier will be suitable for application to the eyes with a polymeric delivery carrier such as but not limited to, an amount of hyaluronic acid. Preparation of suitable ophthalmic solutions requires careful consideration of factors such as isotonicity, the need for buffering agents, the need for preservatives, and sterilization. Lacrimal fluid is isotonic with blood, having an isotonicity value corresponding to that of a 0.9% sodium chloride solution. Ideally, an ophthalmic solution should have this isotonicity value, but eyes can tolerate isotonicity values as low as that of a 0.6% sodium chloride solution and as high as that of a 2.0% sodium chloride solution without substantial discomfort. Some ophthalmic solutions are necessarily hypertonic in order to enhance absorption and provide a concentration of the active peptide strong enough to exert a prompt and effective action. Suitable ophthalmic carriers include ointments, saline solutions, isotonic saline solutions, such as SORBICARE™ (Allergen Pharmaceuticals), NEO-DECADRONT™ (Merck, Sharp, and Dhome) and the like. Suitable ointment bases are typified by a product sold under the trade name LACRILUBE™.

Other suitable ophthalmic vehicles include boric acid, which has a pH slightly below 5.0. Phosphate buffer systems may also be employed and adjusted for isotonicity to provide a choice of pH ranging from about 5.9 to 8.0. Pharmaceutical grade methyl cellulose having a variable viscosity may also be employed.

For vascular treatment, the polymeric delivery carrier will be suitable for application to the vascular wounds with a polymeric delivery carrier such as but not limited to, amounts of hydroxypropylcellulose, hydroxethylcellulose, collagen, and glycerin. Preparation of suitable vascular wound solutions requires careful consideration of factors such as the type of wound, isotonicity, need for buffering agents, preservatives and sterilization. The pH can vary, but usually is in the range of 5.0 to about 8.0. The choice of pH is dictated by the effects on pain and the viability of the surrounding tissue. The preparation of a gel may require gel-forming agents, such as but not limited to, Carbomer 974P, hyaluronic acid, collagen, hydroxypropylcellulose, hydroxyethylcellulose, hydroxymethylcellulose, chondroitin, paraffin, cetyl alcohol, hydrophilic gelatin, dextrin, stearyl alcohol, polyethylene glycol, polyvinyl alcohol, methoxyethylene-maleic anhydride, nanoparticles, liposomes, combinations thereof, modifications thereof and derivatives thereof. In addition, humectants such as but not limited to propylene glycol may be added to attract water into the wound mimicking the role of the dermal glycosaminoglycans and other hydrophilic components of the stratum corneum.

These total delivery systems such as those described above will allow for delivery of substance P to the wound over an extended period of time. This is important since substance P needs to be present in the wound for an extended time in order to orchestrate the cascade of processes that are required in the complex process of wound healing.

In addition to neuropeptides, the compositions of the present invention may include other known growth factors. The term "growth factor" as used herein will be understood to refer to any peptide or protein capable of stimulating cellular proliferation and/or cellular differentiation. Growth factors typically act as signaling molecules between cells. The term "growth factor" as used herein includes cytokines and hormones that bind to specific receptors on the surface of their target cells. Growth factors often promote cell differentiation and maturation, which varies between growth factors. The terms "growth factor" and "cytokine" are used interchangeably herein. Examples of growth factors utilized in accordance with the present invention include, but are not limited to, cytokines, lymphokines, interleukins, chemokines, epidermal growth factor, platelet-derived growth factor, insulin, insulin-like growth factor, transforming growth factor-β, nerve cell growth factor, fibroblast growth factor, platelet-derived growth factor, granulocyte-colony stimulating factor, granulocyte-macrophage colony stimulating factor, neurotropins, erythropoietin, thrombopoietin, myostatin, growth differentiating factor-9, hepatocyte growth factor, and the like.

In certain cases, the presence of the neuropeptide may have a beneficial modulating or potentiating effect on the activity of the growth factor, as described previously in FIGS. 1-3 of U.S. Pat. No. 5,616,562, previously incorporated herein by reference. The concentrations of the other growth factors will generally be from about 0.1 nM to 10 mM, such as from about 0.01 µM to 1 mM, or from about 0.1 µM to 100 µM.

The neuropeptide compositions of the present invention will be useful for treating a wide variety of wounds affecting virtually any tissues of the body. In particular, the compositions will be useful for treating cutaneous wounds affecting the epidermal and dermal layers of the skin, as well as injuries to the cornea and epithelial-lined hollow organs. The wounds may be caused by a wide variety of physical trauma, including but not limited to, cuts, abrasions, thermal and chemical burns, chemical exposure, and the like, as well as from surgical procedures, such as surgical incisions and skin grafting. The wounds may also result from disease including but not limited to, chronic conditions, such as venous stasis ulcers, decubitus ulcers, burns, diabetic ulcers, including keratopathy, idiopathic corneal epithelial defect and other non-healing (trophic) conditions, such as those which occur in denervated regions of the extremities and post penetrating keratoplasty. Viral infections such as metaherpetic keratitis can also cause the wounds.

The neuropeptide compositions of the present invention will find particular use in treating corneal and scleral wounds, including wounds which affect the epithelial layer, stromal layer and endothelial layers of the eye. Heretofore, eye wounds have required particularly lengthy periods to heal and have been subject to numerous complications.

Substance P and the other neuropeptide compositions of the present invention are particularly suitable for promoting wound healing in patients with Substance P deficiency. Especially contemplated is the treatment of cutaneous wounds and non-healing wounds such as occur in diabetes and most especially corneal epithelial wounds in diabetic patients by topical application of compositions containing Substance P.

Vascular Vs. Avascular Wounds

When wounding occurs with vascular injury, tissue factor and intracellular calcium are released, activating factor VII and initiating the extrinsic coagulation cascade. Concomitant reflex vasoconstriction occurs to aid in hemostasis. Hemostasis is ultimately secured by the end product of the coagulation cascade, the fibrin plug. These fibrin fibers become a provisional wound matrix and are the lattice on which platelets aggregate. Activated platelets are the most abundant cells in the wound in the early post injury period. They are sources of proinflammatory substances, such as transforming growth factor-$\beta$ (TGF-$\beta$) and platelet-derived growth factor (PDGF). Activated phospholipase A catalyzes the production of prostaglandins and thromboxane from the arachidonic acid. These substances play central roles in the regulation of vasomotor and platelet activity after injury. Thromboxane A2 helps with hemostasis by its effects of vasoconstriction and platelet aggregation.

After the initial insult and resultant vasoconstriction, vascular permeability is then increased. The classic signs of inflammation are generated by these metabolites. For example, the redness caused by vasodilation is primarily a result of prostacyclin (PGI2). Others include prostaglandin A, prostaglandin D, and prostaglandin E (PGE). Swelling is caused by the leakage of plasma proteins through gaps in the vascular endothelium. This edema is potentiated by PGE2 and prostaglandin F2-alpha (PGF2-alpha). PGI2 and PGE2 promote local blood flow, causing the localized warmth in the area of inflammation, but also allow for entry of inflammatory cells into the wound, which is due to increased vascular permeability.

These cells then release cytokines responsible for fever production. Pain is elicited by the effects of PGI2, PGE, and PGE2 on peripheral sensory nerve endings. Eicosanoids thus exert mediatory actions on the injured tissue's platelet plug formation, vascular permeability, and cellular chemotaxis to influence wound healing. None of the events above would occur in an avascular wound.

Polymorphonuclear leukocytes, which enter the vascular wound at this point in the wound healing temporal sequence, are also involved in avascular wounds. However, their concentration and access to the actual wound are more restricted in an avascular wound such as that found in a cornea.

The next phase in the wound healing process is the proliferative phase of the wound healing. This occurs with fibroblasts moving into the wound. This would happen in both vascular and avascular wounds. From this point on in the wound healing sequence of events both vascular and avascular wounds behave the same with the exception of the effects of angiogenesis that occur in the vascular wound.

Alteration in SP content may represent an underlying defect in diverse wound healing processes which result in impaired maintenance and healing of the corneal epithelium and other tissues which normally contain SP. Substance P deficiency can arise as a result of any of the conditions listed above such as physical trauma, viral infection, neuronal degeneration, diseases which affect neural integrity and metabolic diseases such as diabetes. The deficiency can occur as part of a generalized effect or be specific to a tissue or organ site. Substance P deficiency can also be induced by treatment with capsaicin, which is known to deplete or block the release of SP and affect wound healing. Systemic or topical treatment with enkephalinase, an enzyme that cleaves SP between amino acid residues 6-7, 7-8, and 9-10, can also deplete Substance P. The term "Substance P deficiency" as used herein refers to a condition whereby the level of Substance P within a specific tissue is depleted or is lower than the normal level found in the same tissue in a healthy animal or human. Blockage of the synthesis of Substance P or of its release to its normal site of function, functional blockade e.g. by its antagonist, or the destruction of the substance, either due to disease conditions or artificially induced by treating with drugs and enzymes, can all cause or contribute to Substance P deficiency. Substance P deficient patients can be humans or mammals, including but not limited to, dogs, cats or horses.

For use in wound treatment, the neuropeptide compositions will usually have a concentration in the range described above. The neuropeptide compositions will usually be applied to the affected area periodically, typically from about 2 to about 12 times each day, usually over a period of from about 3 to 14 days, depending on the nature of the wound. In some cases, it may be desirable to apply the compositions indefinitely. The neuropeptide compositions will find particular use in the treatment of wounds resulting from surgery and other intentional interventions where the compositions may be applied immediately after completion of the surgery.

The invention also provides a method for treating wounds in a patient who is Substance P deficient. The method comprises applying a neuropeptide selected from the group consisting of tachykinins, calcitonin gene-related peptide, other sensory nerve neuropeptides, and analogs thereof, such as Substance P or a fragment or analog thereof, to the wound in an amount sufficient to promote healing of the wound.

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

EXPERIMENTAL EXAMPLES

Example 1

Use of Substance P to Treat a Vascular Wound

Substance P exhibits properties which may be capable of stimulating wound healing. Based on this, the purpose of the following example was to evaluate the effect of topically applied substance P on wound healing in full thickness skin punch wounds in a rat model. In addition, selenocystamine was tested as a potential wound treatment at the same time.

Animal Model and General Care

Twenty-one male Sprague-Dawley rats weighing between 300-350 g were used in this study. The rats were housed in the temperature controlled vivarium at Texas Tech Health Science Center with a 12-hour alternating light cycle, and were provided water and rat chow ad libitum. Animals were allowed several days of adjustment upon arrival before the surgery to get rehydrated and familiar with the environment. The study protocol was approved by the Texas Tech University Health Sciences Center Animal Care and Use Committee which assured that the animals received humane care.

Wound Procedure

On the day of the surgery (day 0), the rats were weighed and anesthetized with 1 ml/kg intraperitoneal (IP) injection of the solution made up of 3 parts XYLAZINE® and 7 parts of KETASET®. The animals' backs and necks were shaved and prepared aseptically. Lack of response to tail pinch and absence of a righting reflex were used as indications that anesthesia was adequate. Supplemental anesthetic was administered IP as necessary to maintain an adequate anesthesia.

A 7 mm-diameter punch (George Tiemann & Co.) was used to introduce the punch wound. The procedure was to fold the skin along the sagittal axis and put it down left or right side (rotate animal by animal) against a hard surface, then to thrust the punch through the two layers of skin. In this way, two identical punch wounds were obtained. Four wounds were introduced on each animal. The four wounds were arranged in two columns parallel to the sagittal axis and two rows parallel to the transverse axis.

After the wound procedure, three different treatments were assigned to the wounds. The superior left wound was the control. The superior right wound was assigned to SP treatment. The two under were assigned selenocystamine treatment. For the control wound, a drop of normal saline was applied followed by a layer of AQUAPHOR™ to cover the wound. For the SP wound, a drop of 0.05% (0.5 mg/ml) SP water solution was applied followed by a layer of 0.05% (0.5 mg/g) SP-AQUAPHOR™ to cover the wound. For the selenocystamine wounds, a drop of selenocystamine water solution (10 ug Se/ml) was applied to each wound followed by a layer of selenocystamine-AQUAPHOR™ (10 ng Se/g) to cover the wound. Then gauze and tape were applied to secure the wound. The animals were held under warming lights and observed until they were fully recovered from the anesthesia and then were returned to the vivarium. All the treatment agents and placebo were stored in a refrigerator. Dressing changes and treatments were performed once a day until the animals were sacrificed on day 6. The assignments and dosage of the treatments were as described above.

Following the surgery, the wounds were measured in two dimensions: sagittal and transverse. Photographs were taken using a PENTAX® ESPIO 928 camera and Kodak® ISO 200 color film. After the animals were sacrificed on day 6, the eschars covering the wounds were removed. Then the wounds were again measured in two dimensions, and photographs were taken.

The animals were sacrificed on day 6 after the surgery by euthanasia with SLEEPAWAY® (Sodium Pentobarbital, 7.9% isopropanol, euthanasia solution). The entire wound plus a 1 mm margin of normal skin from each of the test and control wound sites on each animal was excised and preserved in buffered formalin.

The product obtained by multiplying the two measurements of each wound was referred to as the area of the wound. The percentage of the decrease of the wound area on day 6 compared with day 0 was used to evaluate the rate of healing. Since the exact time of wound healing was difficult to determine, day 6 was chosen. At day 6, none of the different treatments had resulted in complete wound healing, yet significant healing had occurred by that time.

Mean and standard deviations were determined on the difference of the percentage of the wound area decrease between each treatment and the control. Significant differences between treatments and the control were determined by paired T-test to see if the percentage of the decrease in wound area was greater for the treated wounds than for the control wound.

Forty-five of the 48 punch wounds on the backs of the rats decreased in size during the six day period allowed for healing. Two wounds did not change in size, and one wound enlarged by 2.9% in the selenocystamine treated wound group. Mean±SE and range of wound size on day 0 and day 6, and mean and range of percent decrease in wound size, are presented in FIG. 1. The slowest healing wound in the SP treated group had at least twice the percent decrease in wound size as did the mean wounds in the other treatment groups. The SP treatment group also had the wound with the greatest decrease in size (66.7%). At 41.6±15.0%, the SP group had the highest % decrease in wound size. For the control there was an average 30.4±11.6% decrease in the wound area over 6 days. For the selenocystamine treatment, the average decrease in wound areas was 31.8±18.3%. Statistical analysis of the data is seen in FIG. 1. Three Paired T-Tests on the decrease percentage of the wound area were conducted: SP vs. control and selenocystamine vs. control. The results indicate that the percentage decrease of the wound area of the SP treated wounds is significantly higher than that of the control wounds ($p<0.025$). However, the percentage decreases of the wound area from the selenocystamine treatments were not significantly higher than the control at the 0.05 level.

Figure 10:
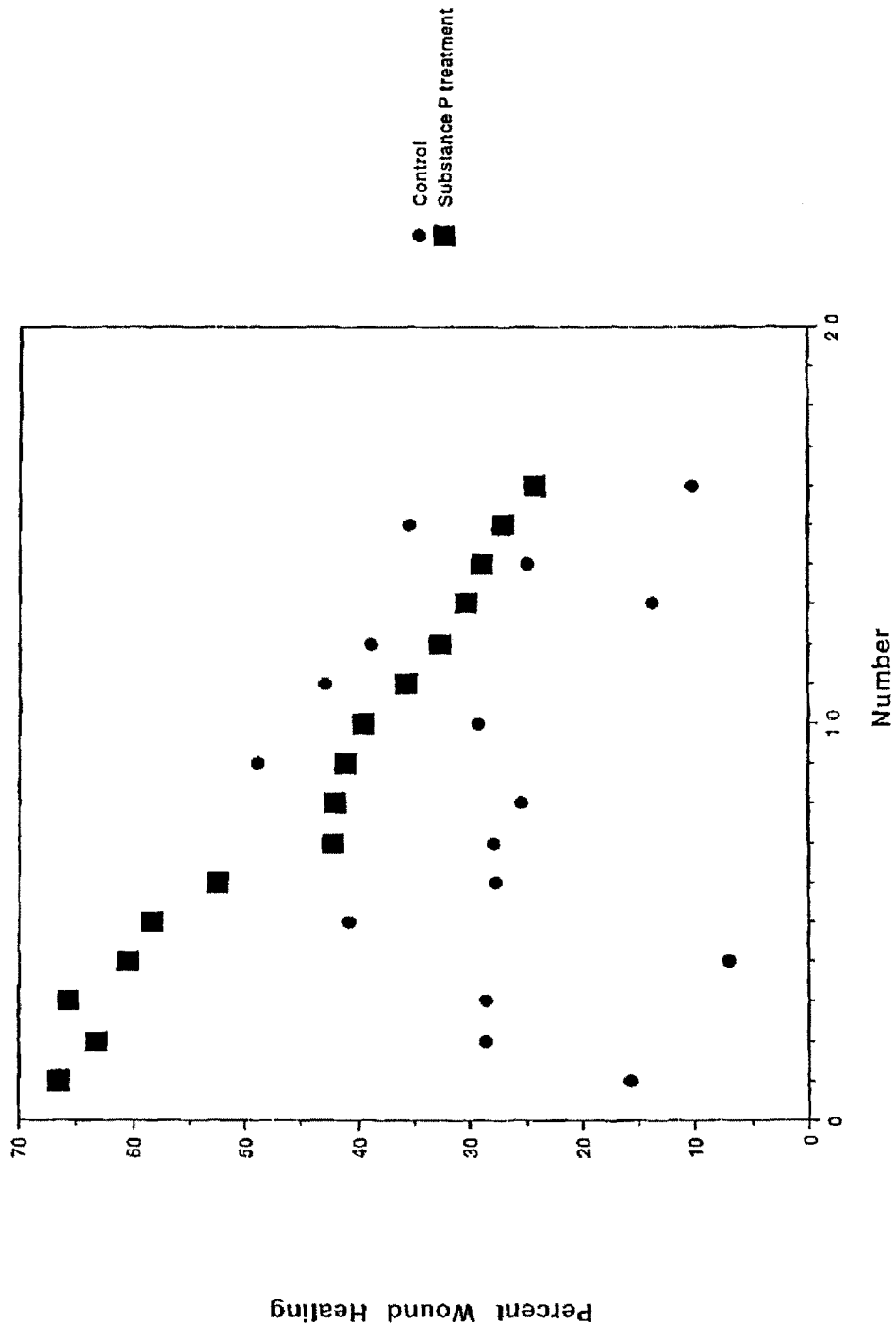
FIG. 10 represents the percent healing after 6 days for a full thickness wound in the back of 16 different rats. The initial wound size was a 7 mm punch wound. Each rat received two wounds, a control (no SP) and an SP treated wound. Both wounds received a hyaluronic acid vehicle. As can be seen, only 4 out of 16 control wound showed more percent healing than the SP wound on the same rat.

Supplemental growth factors have the ability to accelerate wound healing in a variety of experimental animal models (EE). This has even led to clinical trials. However, the human studies have not been as successful as the animal models. Due to the complexity of the interaction of different growth factors, it is likely that the right combination of different growth factors has not been explored. SP has previously been shown to act as a mediator of animal wounds in conditions where the nerves were compromised and in a similar situation in a human patient. The results seen show in a simple rat punch wound model, that the decrease in the wound area of the SP treated wound is significantly higher than that of the control, in a system where SP can be added in a polymeric delivery system where it is released into the wound over an extended period of time (see FIG. 10). This suggests that topical application of SP can accelerate wound healing in an open wound model in which both nerves and tissue have been mechanically damaged, and that the punch model described herein will allow a person of ordinary skill in the art to evaluate the effects of Substance P in conjunction with other growth factors.

The results also show that the decrease in the wound area of the selenocystamine treated wounds were not significantly different from that of the control. This suggests that topical application of selenocystamine did not accelerate wound healing at the concentration used in this study.

Example 2

Effect of SP±IGF-1 in Epithelial Healing after Photorefractive Keratectomy in Rabbits Corneal wound healing after Photorefractive keratectomy and its consequences, epithelial defect and haze, have been studied extensively. Results on how the absence of corneal epithelium affects the stromal keratocytes are contradictory. Some studies showed that an early decrease in the density of keratocytes is followed by an increased number of these cells in the underlying stroma and polymorphonuclear (PMN) inflammatory reaction (Hirst et al., 1981; Kenyon et al., 1979). This stromal change is related to stromal haze and instability of the refractive result. Other studies show that a traumatic removal of the epithelium would prevent changes in the stromal healing (Harmann et al., 1962; Nakayasu et al., 1988).

Studies suggest that the epithelium influences the cellular activation and metabolic activities of stromal cells during wound healing (Dohlman, 1971; Johnson-Muller et al., 1978). Removal corneal epithelium causes loss of the superficial stromal keratocytes in rabbits and monkeys. This keratocyte death may result from osmotic changes that alter the corneal healing process (Campos et al., 1994). The use of corneal preservation medium as a nutrient solution during and immediately after de-epithelialization of rabbit corneas resulted in healthy superficial keratocytes and faster reepithelialization.

The presence of PMN leukocytes in the stroma might be related to the regeneration of the epithelial cells or be stimulated by chemotactic factors liberated by the degenerating keratocytes. The timing of all these findings suggests an interaction not only between the epithelium and keratocytes but also between epithelium and PMN leukocytes. Clinically, this may attribute to melting of the underlying stroma in persistent epithelial defects.

Substance-P (SP) is an eleven residual peptide belonging to the tachykinin family of sensory neurotransmitters. Reid et al (1990; 1993) demonstrate that SP at picomolar levels is mitogenic for ocular epithelial cells. Topical administration of SP in rabbit cornea epithelial defect stimulates DNA synthesis and cell growth. The synergistic effect of SP and IGF-1 has been reported for both epithelial migration and attachment during first phase of epithelial healing (Nishida et al., 1996).

The importance of rapid epithelial healing in improvement of final results after PRK, prompted the evaluation of the effect of topical SP±IGF-1 in epithelial healing after PRK in rabbits.

Material and Methods:

All experiments were conducted according to the Association for Research in Vision and Opthalmology Statement for Use of Animals in Ophthalmic and Vision Research. The protocol was approved by the Animal Research committee of the Texas Tech University Health Science Center.

Excimer Photoablation and treatment protocol: Six New Zealand albino female rabbits weighting between 2-3 kg were anesthetized with intramuscular injection of xylazine hydrochloride (7 mg/ml) and ketamine hydrochloride (40 mg/ml). Topical 0.5% proparacaine hydrochloride was instilled and the eyelids were held open with a wire speculum. After dilation of pupils with a drop of 2.5% phenylephrine and 1% tropicamide, the animals underwent a bilateral combined chemical (18% alcohol for 45 seconds) and mechanical corneal de-epithelialization for 9.0 mm. Both corneas then received 193 nm Excimer laser using Ladder Vision laser with an 8.0 mm ablation zone and a depth of 70.0 μm (−3.00 myopic correction). At the conclusion of the laser treatment, a drop of 2% sodium fluorescein solution was instilled in the conjunctival culde sacs, and corneal epithelial defects were assessed and documented using digitized images. Then one drop of combined Substance-P (250 μg/ml) and IGF-1 (25 ng/ml) in a hyaluronic acid vehicle (14 mg/ml) was instilled in the right eyes. The left eyes did not receive any treatment and were used as control eyes.

Postoperative Regimen and follow up: Postoperatively, one guttae of combined Substance-P (250 μg/ml) and IGF-1 (25 ng/ml) in sodium hyaluronate vehicle (Haelon G V, Pharmacia, 14 mg/ml) instilled in the right eyes twice a day, and corneal epithelial defects were assessed and documented using digitized images before each treatment in both eyes. After initial healing, the epithelial defects in the control eyes regressed at day 3, and due to humane reasons, it was decided to treat the control eye (left eye) according to treatment protocol for the right eye until complete healing. All rabbits were then killed at 6 weeks of treatment and sent for pathology in Bowins solution.

Statistical Analysis: An exponential recovery model was performing for analyzing the rate of healing over the initial 100 hours. The wound size was expressed as a percentage of maximum. This model of analysis was performed at the beginning because it makes the fewest assumptions. However, the exponential recovery model could not fit the treated-eye results very well because the main difference in healing rate occurred between 30-70 hours. The data was reanalyzed based on a two-component model of healing rate in the following ways: (1) the initial data was normalized with respect to the initial value from the same eye (in contrast to group mean); and (2) the regression line converged to 100% at 1 hour (instead of 0 hours). After taking the median of all 6 rabbits, it was demonstrated that the results for treated and non-treated eyes were very similar during the first 30 hours, and the main difference in healing rate occurred between 30-70 hours (FIG. 2).

For analyzing the results of epithelial detachment in corneal histologies, a Chi-Square Test analysis was used.

Results:

Epithelial defects created by chemical and mechanical techniques healed uneventfully in all treated eyes with an average healing time of 85.5 hrs. Two of the non-treated eyes (left eye) developed persistent epithelial defects, and one of the non-treated eyes (rabbit #3) also showed difficulty in the final central healing process. The average healing time for non-treated eyes was 126.4 hrs (FIG. 3). The healing time in rabbits with persistent epithelial defect was calculated based on the healing time that would be expected based on a normal healing process.

The initial rate of epithelial healing demonstrates that the result for treated and non-treated eyes were very similar during the first 30 hours, and the main difference in healing rates occurred between 30-70 hours after treatment (FIG. 2). Statistical analysis of the rate of the second process suggests a difference in healing rates (p value=0.053857; Confidence Interval: −0.00058243 0.048491), but is not statistically significant (paired-T, p>0.05, df=5).

Histology studies: All rabbits were killed 6 weeks after PRK, and corneal samples were sent for pathology. There were two major histology findings: (1) sub-epithelial pannus of collagen and spindle cells, and (2) epithelial non-attachment.

In rabbit #1 there was minimal sub-epithelial pannus formation and no epithelial separation in both treated and non-treated eyes. In rabbit #2 there was moderate sub-epithelial pannus formation in both eyes, but there was an area of epithelial separation in the central cornea in the left eye (non-treated eye). In rabbit #3 there was severe sub-epithelial pannus formation with no epithelial separation in both eyes. But non-treated eye showed a localized area of thick sub-epithelial pannus in the central cornea with evidence of atrophy in the overlying epithelium but no epithelial separation. In rabbit #4 there was moderate sub-epithelial pannus formation in both eyes with a zone of epithelial separation within the pannus in right eye and broad epithelial separation in the left eye.

In rabbit #5 a minimal sub-epithelial pannus of collagen and spindle cells and no evidence of epithelial separation were noticed in the right eye, while in the left eye severe pannus formation and localized epithelial separation with separated clefts within the pannus was prominent. And finally in rabbit #6 there was severe pannus formation and epithelial separation in the right eye and moderate pannus formation with no evidence of epithelial separation in the left eye.

In summary the pathology results show that in 3 out of 6 non-treated eyes there is evidence of epithelial separation, and also in one non-treated eye, there is an area of sub epithelial atrophy, which can predispose the epithelium for separation. Only in one treated eye was epithelial separation noticed, which is consistent with longer epithelial healing in that eye. These results were analyzed statistically, and although the result was not statistically significant (P=0.31891 for $x^2$=2.2857 with df=2), the number of studied eyes may have influenced the results, which demands further evaluation.

Discussion

The wound in the denuded corneas shows an intensive inflammatory response and an absence of keratocytes (Campos et al., 1994; Hanna et al., 1989; Campos et al., 1994). The phenomenon of epithelial-loss-induced keratocyte loss has recently been characterized as a process of apoptosis (Gao et al., 1997) and is speculated to be mediated by interleukin-1 (IL-1) elaborated by epithelial injury (Wilson et al., 1996), and reactive oxygen free radicals generated by excimer laser irradiation (Hayashi et al., 1997), and acute inflammatory cells. Besides, this keratocyte death may result from osmotic and metabolic changes of stromal cells related to epithelial denuation (Campos et al., 1994).

The presence of PMN leukocytes in the stroma might be related to the regeneration of the epithelial cells or be stimulated by chemotactic factors liberated by the degenerating keratocytes. The timing of all these findings suggests an interaction not only between the epithelium and keratocytes but also between epithelium and PMN leukocytes. Clinically, this may attribute to melting of the underlying stroma in the persistent epithelial defects.

These changes can cause photoablated corneal wounds to undergo a transitional stage of epithelial hyperplasia and stromal keratocytes proliferation, which in turn leads to corneal scaring and haze in the late stage (Tuft et al., 1993).

The cornea is more densely innervated with sensory nerve fibers than any other tissue in the body. There is statistically significant less hemidesmosome formation up to 12 weeks in corneas after mechanical de-epithelialization with or without PRK (Chang et al., 1996), and it will affect epithelial adhesion complex and corneal barrier function (Chang et al., 1996; Gibson et al., 1989). These changes may be due to sensory denervation of the cornea following PRK, which can affect epithelial healing and cellular adhesion (Sigelman et al., 1954; Araki et al., 1994).

In the cornea, a dense network of SP positive nerve fibers has been reported (Miller et al., 1981; Shimizu et al., 1982). SP is a constituent of sensory nerve fibers and has been postulated to mediate various physiologic functions (McGills et al., 1987). It has a key role in the ocular neurogenic responses to various stimuli (Shimizu, 1982; Nishiyama et al., 1981). The SP level in the cornea of adult mouse is reduced 40% by denervation of the trigeminal nerve (Keen et al., 1982).

Also, presence of a receptor for SP has been reported in corneal epithelial cells (Kieselbach et al., 1990; Denis et al., 1991). It also has been shown that there is a synergistic effect between SP and IGF-1 in epithelial migration (Nishida et al., 1996). SP or IGF-1 alone does not influence the migration of the corneal epithelial cells. This synergistic effect can be nulled by the addition of an SP receptor antagonist, thus suggesting that the synergistic effect of SP with IGF-1 is mediated by SP receptors in the corneal epithelium (Nishida et al., 1996).

A continuous renewal through the active repair system is one of the most important mechanisms for the maintenance of epithelial integrity. During this process, migration and cell adhesion are the most important processes (Grinnell et al., 1990). There are three phases involved in the process of corneal healing; migration of corneal epithelial cells and forming a monolayer of epithelial cells (first phase), proliferation of monolayer epithelial cells (second phase), and differentiation to well-differentiated epithelial cells (third phase) (Nishida, 1993).

The synergistic effect of SP and IGF-1 has been reported for both epithelial migration and attachment during the first phase of epithelial healing (Nishida et al., 1996). Treatment of the corneal epithelial cells with SP and IGF-1 stimulate the attachment of cells to various extra cellular material proteins (Nishida et al., 1996). The mechanism for action of the SP+IGF-1 might be mediated by the up regulation of fibronectin receptor in the corneal epithelial cells. SP also stimulates DNA synthesis in rabbit corneal epithelial cells (Reid et al., 1993).

As mentioned before, the cornea is heavily innervated with sensory nerve fibers, and these innervations play an important role in the maintenance of normal structure and function of the cornea. Many studies have demonstrated a correlation between reduced SP level in the cornea and denervation of the trigeminal nerve to the eye (Keen et al., 1982; Butler et al., 1980; Unger et al., 1981). These clinical observations and laboratory studies strongly suggest that neuropeptides such as SP may play an important role in the physiology of corneal epithelial cells and their healing process. As observed in the present invention, the main difference in healing rate between treated and non-treated eyes occurred between 30-70 hours after PRK. This timing correlates with the time that the first layer of epithelial cells already migrate to the denuded area and are ready to proliferate. The effect of SP+IGF was thus expected to be shown around this timing, the time for epithelial attachment and proliferation. The effect of SP+IGF on epithelial migration, attachment and proliferation has aided the process of epithelial healing to be faster and smoother in treated eyes. Although this difference is not statistically significant (P value=0.053857), considering the number of studied eyes (6 rabbits, 12 eyes) and the proximity of the P value to a significant level, this demands further study end evaluation in this matter.

The addition of HA to the composition used in Example 2 increased the dwell time of the composition of the present invention. Previously, Substance P compositions were administered as one drop every 15 minutes for two hours, and this was performed twice a day (see for example, Brown et al. (1997) Archives of Ophthamology, 115:926-927; and Lee et al. (2002) Archives of Ophthamology, 120:215-217). In Example 2, the compositions comprising Substance P and IGF-1 with an HA polymeric delivery vehicle only required one drop administered twice a day. Therefore, the compositions of the present invention demonstrate that the polymeric delivery carrier increases the dwell time of the neuropeptide present in the composition such that the number of required administrations is reduced when compared to the number of required administrations of compositions containing neuropeptide alone.

Example 3

Substance P Analogs

As mentioned previously, Substance P (SP) is a ubiquitous mammalian neuropeptide having the structure RPKPQQFF- GLM (SEQ ID NO:1). In order to determine which portion of SP is responsible for its binding to the NK1 receptor, physiological assays have been performed using SP analogs that were systematically shortened, and it was found that the six amino acids at the carboxy terminal end of the molecule were required for most of SP's binding to its receptor: $SP_{6-11}$ (SEQ ID NO:8) showed activity of about 50-90% of that which was found for the whole SP molecule. Of the six C-terminal residues, the importance of the phenylalanine residues at positions 7 and 8 for the SP–NK1 receptor interaction was demonstrated by the finding that the substitution of another amino acid for either of these residues results in a dramatic change in reactivity. For example, replacement of either $Phe^7$ or $Phe^8$ by a D-phenylalanine residue results in a 20-fold decrease in the binding of the SP analog to NK1, and a D-phenylalanine substitution at both the 7 and 8 positions causes a 400-fold decrease (Wang, et al. (1993) Regulatory Peptides, 44: 269-275). In contrast, the replacement of all of the first four amino terminal residues in SP by the corresponding D amino acids results in only a 20-fold reduction in binding. Substitution of the first five residues by D amino acids causes a 70-fold reduction.

The importance of the $Phe^7$ and $Phe^8$ residues of SP, particularly the phenyl ring moieties, for binding between SP and the NK1 receptor is also suggested by the structures of the antagonists that have been shown to be selective for the NK1 receptor. For instance, in the antagonist RP 67580, substitutions at the qem-diphenyl moiety result in a loss of the antagonist activity, while substitutions at the ortho position on the phenyl ring or substitutions on the benzylic carbon result in increased affinity for the NK1 receptor. A notable presence of aromatic (benzene and/or indole) rings is also found in the SP antagonists CP-96,345 (Lowe (1992) Drugs of the Future 17:1115-1121), FK888 (a phenylalanine-containing tripeptide) (Fujii, et al. (1992) Br. J. Pharmacol. 107: 785-789), WIN 66306 (a heptapeptide) and Hirschmann's SP antagonist (Hirschmann, et al. (1992) Am. Chem. Soc. 114: 9217-9218), all effective competitive inhibitors of SP-NK1 binding. Thus it appears that an interaction between the phenylalanine sidechains in SP and the NK1 receptor is crucial to the biological activity of substance P. Given that the NK1 receptor is a membrane-bound protein, it is therefore likely that SP in general, and the phenylalanine residues of SP in particular, interact with its receptor in a hydrophobic environment.

An interaction between the phenylalanine residues in SP and hydrophobic sites on the NK1 receptor is implied by the results of Woolley and Deber (1987), who characterized the complexes formed between substance P and sodium dodecylsulfate, lysophophatidylglycerol, or lysophosphatidylcholine micelles. Red shifts in the UV spectra of the phenyl rings in such peptide-micelle preparations indicated an increased hydrophobic environment for these residues. CD and NMR spectroscopy of SP in these micelles also implied that the lipid environment affected the conformation of SP, relative to its conformation in solution. Young et al. (1992) found, from nuclear Overhauser effects (nOe) observed using nuclear magnetic resonance spectrometry, that the phenylalanine residues of SP are inserted into the hydrophobic core of SDS micelles.

Recently, Young, et al. (Biopolymers, 34:1449-1462 (1994)) have reported a structure, based on nOe measurements of SP in aqueous SDS micelles and molecular modeling, which indicates that SP assumes a $3_{10}$ helix conformation from residues $Pro^4$ through $Phe^8$ in this membrane-like environment. Such a helical structure was also indicated by Convert, et al. (Neuropeptides, 19:259-270 (1991)) from NMR studies of SP in methanol.

In order to better assess the role of the phenylalanine residues of SP in SP-NK1 interactions, it was determined whether the synthesis of SP analogs with a methyl group substitution for either the pro-R or the pro-S hydrogen on the beta carbon of L-phenylalanine would represent the most subtle change which could be made to the SP molecule while restricting the conformational positioning of the phenylalanine side chains. The resulting β-methylphenylalanine (β-MeF)-containing substance P analogs (where either the R-β-MeF or the S-β-MeF diastereomers of the L-phenylalanine residues are employed) could then be investigated using physiological smooth muscle contraction assays, NMR spectrometry, and molecular modeling, with the ultimate goal of ascertaining a predictable trend between the spatial orientation of the $Phe^7$-$Phe^8$ moiety of SP and the biological activity of the peptide. The use of β-MeF residues to probe the conformational aspects of peptide activity has been used by Hruby, et al. (1991) for enkephalin, by Huang et al., (1992) for somatostatin, and this technique has been discussed at some length by Kover, et al. (1994).

The biological assay chosen for this study was smooth muscle contraction with the rabbit iris sphincter. This tissue was chosen because the tachykinins SP, NKA, and NKB appear to act on the rabbit iris sphincter muscle directly without the involvement of nerve-mediated release of secondary myotropic substances, which could complicate the interpretation of the results and because the NK2 receptor does not appear to be present (Too et al., 1988). The conformational investigations involved $^1$H-NMR analyses of a set of β-MeF-containing SP analogs, and a computational study of the effects that the introduction of a β-methyl group in the $Phe^7$ and/or $Phe^8$ residues has upon an energy minimized structure of the peptide, using the helical structure of SP derived by Young et al. (1994) as a starting point for the calculations. The results of this study demonstrated that substitutions of p-MeF residues for Phe residues in SP result in changes in the biological activity of the peptide which varies from a five-fold enhancement in activity to a fifteen-fold diminution in activity. β-MeF substitutions do not drastically alter the backbone conformation of the peptide, but sidechain-sidechain steric repulsions caused by substituting the Phe residues of SP by β-MeF residues tend to result in slight backbone conformations which alter the spatial orientation of the Phe sidechains. Overall, these results suggest that the maintenance of a trans sidechain conformation of the $Phe^8$ residue in SP, relative to a $3_{10}$ helical backbone structure, is necessary for the maintenance of the smooth muscle contraction agonist properties of substance P.

(2S,3S)-β-Methylphenylalanine and (2S,3R)-β-Methylphenylalanine were synthesized using the method of Dharanipragada, et al. (Tetrahedron 48: 4733-4748 (1992)). The N-fluorenylmethoxycarbonyl (FMOC)-protected derivatives of each amino acid, which have not been reported before, were prepared using the following representative procedure (Lepatsanis, et al., 1983): (2S,3S)-β-Methylphenylalanine (203 mg, 0.94 mmol) was stirred in 9% aqueous sodium carbonate (3.4 mL) at 0° C. and N-(9-fluorenylmethoxycarbonyloxy)-succinimide (266 mg, 0.788 mmol) in dioxane (2 mL) was added. After stirring at room temperature for 1 h, water (20 mL) was added, and the solution was extracted with ether (3×10 mL). The aqueous phase was then acidified with 10% HCl and extracted with ethyl acetate (3×10 mL). The ethyl acetate extracts were dried over $MgSO_4$, filtered, and concentrated to give the crude (~90%) product, which could be further purified by flash chromatography on silica gel using ethanol/chloroform (5:95) as the eluent to give 194 mg (60%) of pure N-Fmoc-(2S,3S)-β-methylphenylalanine: $^1$H NMR (CDCl$_3$) δ1.38 (d, J=7.0 Hz, 3H), 3.44 (dd, J=6.8, 5.6 Hz, 1H), 4.19 (t, J=6.8 Hz, 1H), 4.29-4.51 (m, 2H), 4.62 (dd, J=8.9, 5.0 Hz, 1H), 5.0 (d, J=9.0 Hz, 1H), 7.11-7.46 (m, 9H), 7.46-7.60 (m, 2H), 7.76 (d, J=9.0 Hz, 2H); $^{13}$C NMR (CDCl$_3$) δ 17.80, 41.75, 47.09, 58.94, 66.90, 119.92, 124.95, 127.03, 127.37, 127.68, 128.62, 140.24, 141.27, 143.59, 156.30, 176.43; IR (neat film) 3650-3130, 3130-2840, 2341, 1710, 1514 cm$^{-1}$. HRMS m/z 401.1631 (calculated for C$_{25}$H$_{23}$NO$_4$ [M$^+$], 401.1627). This procedure was followed using (2S, 3R)-β-methylphenylalanine to yield N-Fmoc-(2S,3R)-p-methylphenylalanine in 71% yield: $^1$H NMR (CDCl$_3$) δ 1.40 (d, J=6.4 Hz, 3H), 3.34 (t, J=8.4 Hz, 1H), 4.11-4.50 (m, 3H), 4.62 (dd, J=8.4, 5.2 Hz, 1H), 5.39 (d, J=8.8 Hz, 1H), 7.11-7.48 (m, 9H), 7.48-7.52 (m, 2H), 7.18-7.32 (m, 2H); $^{13}$C NMR (CDCl$_3$) δ 16.17, 42.09, 47.13, 59.14, 67.11, 120.00, 125.03, 127.10, 127.29, 127.74, 128.52, 140.89, 141.30, 143.72, 155.89, 175.84; IR (neat film) 3636-2813, 2359, 1714, 1515 cm$^{-1}$. HRMS m/z 401.1628 (calculated for C$_{25}$H$_{23}$NO$_4$ [M$^+$], 401.1627).

The eight substance P analogs bearing each of the β-methylphenylalanine residues in positions 7 and/or 8 were synthesized from the FMOC-protected amino acids. The sidechain protecting groups for the trifunctional residues Arg[1] and Lys[3] were the Pmc and Boc groups, respectively. The peptides were prepared by solid phase synthesis on a Rink resin using HBTU chemistry procedure using a Protein Technologies, Inc. Symphony peptide synthesizer. The peptides were cleaved from the resin with a TFA cocktail (4% thioanisol, 4% thiophenol, and 4% EDT) for 1.5 hours at room temperature, then purified using preparative HPLC (C$_{18}$, 300 Å, 21.4 mm×25 cm, 5 μm spherical packing at a flow rate of 10 mL/min), with UV detection (214 nm). Two HPLC mobile phases, solution A (5% deionized water in acetonitrile containing 0.1% of TFA) and B (5% acetonitrile in deionized water containing 0.15% TFA) were used in a programmed gradient of 5-70% A over 60 min. The purity of each peptide was checked by analytical HPLC (C$_{18}$, 300 Å, 4.6 mm×25 cm, 5 μm spherical packing at a flow rate of 1 mL/min, same mobile phase as for the preparative runs). In order to verify the identity of the synthetic substance P analogs, fast atom bombardment (FAB) mass spectra were measured for each peptide (FIG. 5).

New Zealand White rabbits were sacrificed by an i.v. overdose of sodium pentobarbital. The eyes were then enucleated and the iris/ciliary body was isolated. Central regions of the iris sphincter muscle was then isolated and the tissue bisected, producing two iris sphincter muscle preparations. The muscle strips were connected to a Grass force-displacement transducer with an initial loading force of 100 mg placed on the muscle. The tissue was then allowed to equilibrate for 60 minutes. Contractions were recorded by a Grass 7 Physiograph. Tissues were bathed at 37° C. in a 50 ml modified Ringer's solution (90 mM NaCl, 3.6 mM KCl, 20 mM HEPES (sodium salt), 0.6 mM MgCl, 7.5 mM Na$_2$SO$_4$, 1.4 mM Ca-gluconate, 20 mM NaHCO$_3$, 0.6 mM MgSO$_4$, 0.6 mM K$_2$HPO$_4$ and 26 mM glucose). The Ringer's solution was gassed with 95% air/5% CO$_2$ (pH 7.4). To suppress the endogenous production of prostaglandins which have been shown to contract the iris sphincter muscle, the incubating solutions contained indomethacin at a concentration of 1 μg/ml. To block potential proteolytic effects the following proteolysis inhibitors were added: 1 μM thiorphan, 1 μM phosphoramidon, 1 μM captopril, 3 μg/ml leupeptin, and 3 μg/ml chymostatin.

To evaluate the viability of each muscle preparation, maximum contraction was determined by a 10$^{-5}$ M dose of carbachol at the beginning and end of each experiment. Following the initial carbachol dose, tissues were washed by three exchanges of Ringer's solutions. Previous studies have shown that this is sufficient to remove carbachol from these solutions and to return the resting tension to normal values. Each peptide was then evaluated for its ability to induce sphincter muscle contraction, and dose-response curves (from 2×10$^{-11}$ to 7×10$^{-7}$ M) were determined. A minimum of four determinations were performed for each experimental condition. The dose response curves were fit by means of a nonlinear regression analysis program (Sigma Plot®, Jandel Scientific). The following equation was used to analyze the data: $R=100[A]^H/([A]^H+EC_{50})$, where R is the percent maximal response, A is the agonist dose, $EC_{50}$ is the agonist concentration producing a half-maximal response, and H is the Hill coefficient.

$^1$H-NMR data for the four monosubstituted βMeF-substituted SP analogs were obtained using a Brucker AF-300 spectrometer (300 MHz). Samples were prepared by dissolving 4 mg of the peptide in 0.5 mL of CD30H, giving a 3 mM solution. Proton assignments were made by analogy to published assignments for SP (Young, et al, 1994) and from the COSY spectra (Young et al., 1994).

Computations were carried out using the QUANTA/CHARMm programs (Molecular Simulations, Inc.) on a Silicon Graphics Indigo workstation. Starting with the atomic coordinates for the structure of SP in aqueous SDS micelles kindly provided by professor Rickey Hicks (Young, et al., 1994), a methyl group was introduced to replace either the pro-R or the pro-S hydrogen of the 13 carbon of Phe[7] and/or Phe[8] in this structure. A radially dependent dielectric of 32 was used to approximate an environment similar to that used in the NMR studies (Young, et al., 1994; Convert, et al., 1991). A dihedral angle grid search of the $\chi_1$ angle was conducted systematically at both Phe[7] and Phe[8] for each of the analogs. The conformations were searched at a 30° resolution, to insure that all the probable staggered conformations were examined. The resulting conformers were then minimized. To insure full convergence for each conformer, 500 steps of Steepest Decents and 1000 adjusted basis Newton-Raphson steps were performed to minimize the structure. This minimization strategy was sufficient to obtain complete convergence for each of the minimized structures. The Boltzman distributions for the $\chi_1$ dihedral angles of the Phe[7] and Phe[8] sidechains in the minimized structures were then calculated to determine the relative populations of the trans, gauche(−), and gauche(+) conformers at the phenylalanine residues.

The structures and shorthand designation for the eight βMeF-substituted SP peptides studied are indicated in FIG. 5. The eight synthetic peptides used in these studies were found to be of 94-99% purity in each case.

Figure 6:
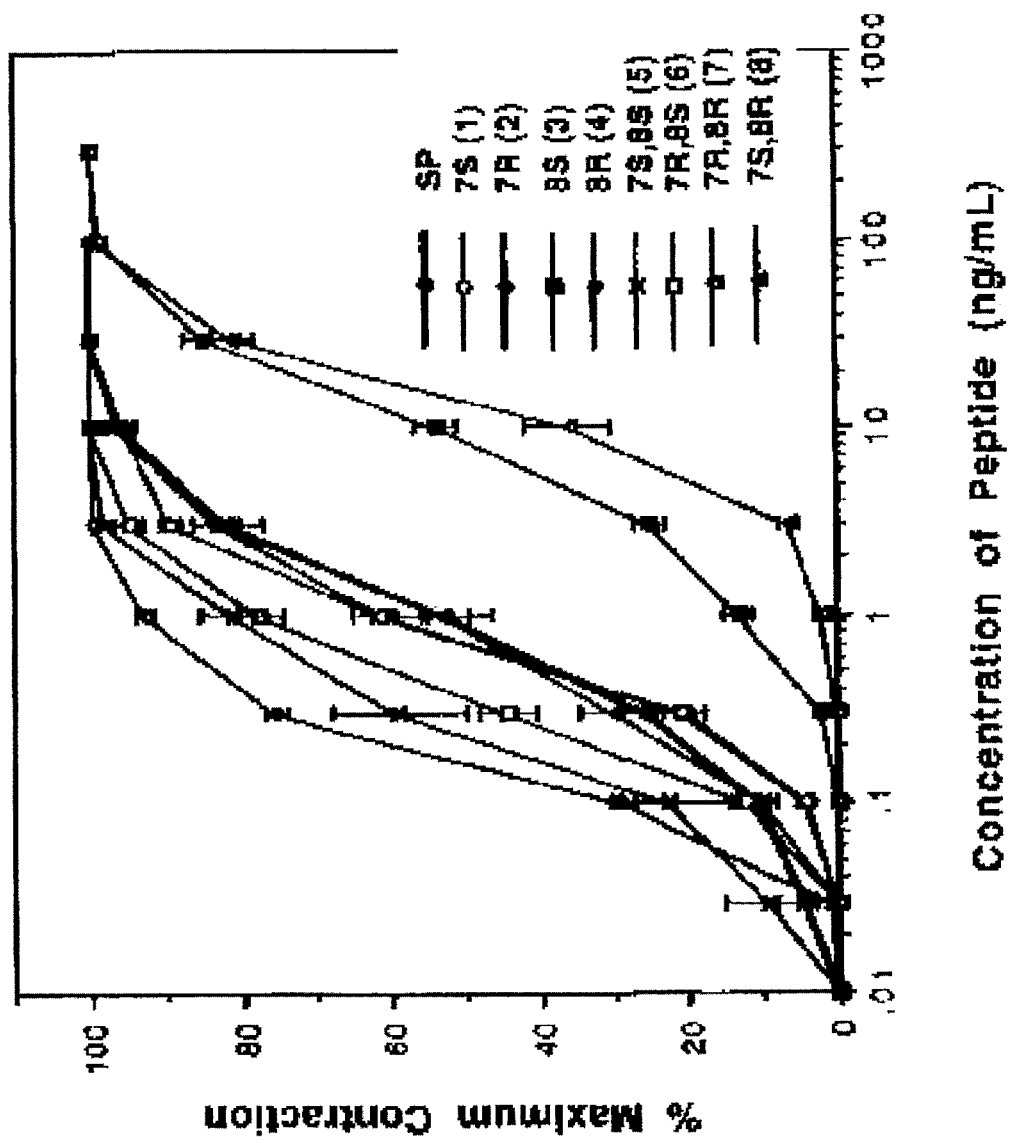
FIG. 6 represents data comparing dose-response curves for SP and the βMeF-containing SP analogs 1-8.

FIG. 6 demonstrates that the addition of SP at doses greater than 10$^{-10}$ M produces a rapid increase in the force of contraction of the rabbit iris sphincter muscle. This increase was dose-related, with a maximum effective dose of 10$^{-7}$ M. These values are in agreement with those found for SP in this and other tissues. Subsequent washing of the tissue demonstrated that this contractile response was fully reversible (data not shown). The presence of either R- or S-β-methyl groups on one or both of the phenylalanine residues of SP, in the eight βMeF-containing synthetic peptides, results in varying activities in this assay, yielding muscle contraction responses that range from 0.15 to 10 nM for the concentration at half maximal contraction ($EC_{50}$). According to these $EC_{50}$ values, the rank order of potency for the eight βMeF-containing SP analogs and SP are:

8R-(βMeF)SP>7S,8S-(βMeF)$_2$SP>7R,8S-(βMeF)$_2$SP>7S-(βMeF)SP>7S,8R-(βMeF)$_2$SP>7R-(βMeF)SP>SP>8S-(βMeF)SP>7R,8R-(βMeF)$_2$SP.

Each dose-response curve represents a total of eight separate muscle preparations, and a standard deviation of less than 15% was observed for these data.

NMR Studies. $^1$H NMR spectra of the four SP analogs containing single βMeF substitutions were obtained, and the chemical shifts of selected protons are reported in FIG. 7. Most portions of the spectra were similar to the spectrum of SP, indicating that the β-methyl substitutions did not drastically alter the overall solution structure. However, local changes in the signals for protons as far as three residues removed from the site of the βMeF substitution were observed. For example, β-methyl substitution at either Phe$^7$ or Phe$^8$ resulted in a change in the chemical shifts of the α and β protons on both Glu$^5$ and Glu$^8$, as well as a change in the chemical shifts of both α protons on Gly$^9$. These changes were accompanied by changes in the shifts of the protons located on the Phe residues (7 and 8), as expected. Qualitative changes in the $^1$H-NMR signals of the aromatic protons in the βMeF-containing analogs, relative to SP, were also observed. This indicated that the βMeF substitutions affected the orientation of the phenyl rings, and thereby altered their environment.

Among the βMeF-containing SP analogs, the most striking changes in the $^1$H-NMR spectra, relative to SP, occurred in the case of 8S-(βMeF)SP, where the greatest changes in the chemical shifts for the Gln$^5$ and Gln$^6$ α and β protons and the Phe$^7$ α hydrogen were observed. This suggests that the substitution of an S-βMeF residue for Phe$^8$ results in the most significant change in the conformation of the local N-terminal region (Gln$^5$, Gln$^6$, Phe$^7$) observed for any of the monosubstituted analogs.

In the $^1$H NMR spectrum of each of the monosubstituted βMeF-substituted SP analogs, the observed coupling constant between the α and β hydrogens on the β MeF residue is greater than 8 Hz. This is consistent with an average side chain conformation in which these two protons are anti to each other, as expected for the trans and gauche(−) conformations predicted to be favored in the R- and S-βMeF sidechains, respectively (Kover, et al. (1994) J. Org. Chem., 59: 991-998).

For all of the substance P analogs, the presence of one or more β methyl groups in the phenylalanine residues resulted in minimized structures which retained 3$_{10}$ helical backbone conformations similar to that of substance P obtained by Young, et al. (1994), which served as the starting point for the minimizations. The most significant variations in the backbone conformations of the βMeF-containing SP analogs occurred at the phenylalanine and adjacent residues.

Figure 8:
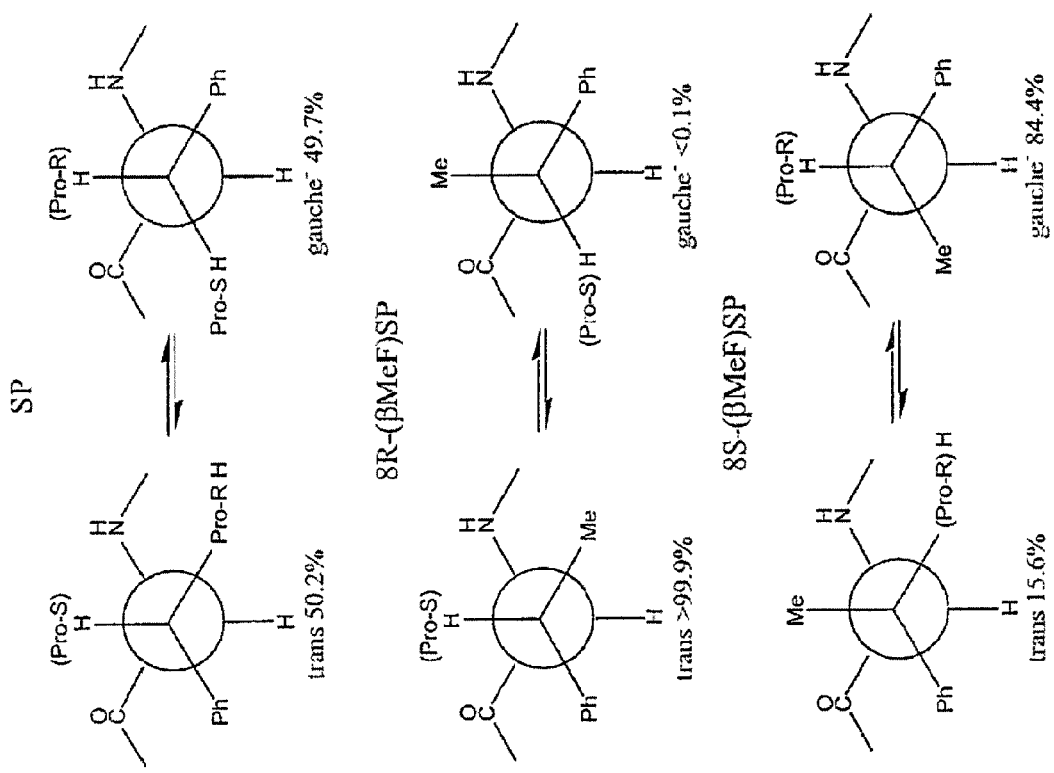
FIG. 8 represents the Boltzman distribution of orientations of the Phe 8.

More significant variations occurred (in some cases) in the sidechain conformations of the Phe$^7$ and Phe$^8$ residues in the minimized structures of the various βMeF-substituted SP analogs. These variations are indicated in FIG. 8, which lists the Boltzman distributions of the staggered sidechain dihedral angles ($\chi_1$) for the Phe$^7$ and Phe$^8$ residues in SP and each βMeF-substituted analog. None of the peptides favored the gauche(+) conformation at either residue to any extent. In substance P, the trans conformation is exclusively favored at Phe$^7$, while the trans and gauche(−) conformations are equally favored at Phe$^8$ (FIG. 9). In the minimized structures of the monosubstituted βMeF-containing SP analogs, the trans conformation of Phe$^7$ is still favored, but the conformation of the $\chi_1$ angle of Phe$^8$ is biased in favor of the trans conformation in 7S-(βMeF)SP and in 8R-(βMeF)SP, and the $\chi_1$ angle of Phe$^8$ is biased in favor of the gauche(−) conformation in 7R-(βMeF)SP and in 8S-(βMeF)SP. In the minimized structures of the disubstituted βMeF-containing SP analogs, the trans conformation of Phe$^7$ is favored for all but the 7R,8S-(βMeF)$_2$SP analog, where the gauche(−) conformation at Phe$^7$ is highly favored. Also, among the disubstituted analogs, the trans dihedral conformation is favored at Phe$^8$ in the 7R,8R- and 7S,8R-(βMeF)$_2$SP analogs, while the gauche(−) conformation is favored at Phe$^8$ in the 7R,8S- and 7S,8S-(βMeF)$_2$SP analogs.

Using selective agonists for the NK1, NK2, and NK3 receptors and an NK1 selective antagonist, Wang and Hakanson (Regulatory Peptides, 44: 269-275 (1993)) found that the iris smooth muscle contains NK1 and probably NK3 receptors, but no NK2 receptors. With different agonists and antagonists, Hall et al. (1993) also determined that it was NK1 and NK3 receptor activation which resulted in contraction of the rabbit iris sphincter. Therefore, since the binding of SP to the NK1 and NK3 receptors in the rabbit iris differs by a factor of over 20, it is reasonable to assume that the contraction of the rabbit iris sphincter by βMeF-containing SP analogs primarily reflect the activation of the NK1 receptor.

The use of β-methylphenylalanine residues to probe conformational aspects of peptide-receptor interactions is well known. Kover, et al. (1994) found that βMeF substituents affected the backbone conformation of a cholecystokinin subunit peptide only locally, at the amino acid residues adjacent to the βMeF residue. The NMR studies of the monosubstituted βMeF-containing SP analogs indicated a similar localized effect: the $^1$H-NMR spectra of the monosubstituted βMeF-substituted SP peptides in methanol indicate that the global conformation of SP is not drastically altered upon introduction of a βMeF residue, and βMeF substitutions appear to restrict the sidechain conformation at the residue and to perturb the chemical environment of the residues adjacent to the substitutions. The modeling studies also support this observation, as the overall 3$_{10}$ helical structure of SP, used as the starting point for the calculations, was not drastically altered upon introduction of the β-methyl groups.

The molecular modeling experiments suggest that each of the βMeF-containing SP analogs favors a set of conformations which vary in the manner in which they project the phenyl-bearing sidechains, and in some cases a correlation exists between the preferred conformation and the interaction of the SP analog with the NK1 receptor, as judged by the rabbit iris sphincter muscle contraction assay. Possible insights into the effects which the various βMeF substitutions exert upon the conformation of SP, especially in the monosubstituted analogs, can be revealed by examining the Newmann projections of the adjacent Phe sidechains from a viewpoint which presents the two sidechains as if they were coplanar. (In fact, the 3$_{10}$ helical structure of SP, maintained in the analogs, orients these two sidechains in such a manner, only "splayed" away from the coplanar presentation).

In SP, there exists a bias in favor of the trans conformation at Phe$^7$, which is attributed to steric effects exerted by the Pro$^4$, Gln$^5$, and Gln$^6$ residues of the helix, but no bias in favor of a specific conformation at Phe$^8$. In 8R-(βMeF)SP, the most active SP analog, the trans bias at Phe$^7$ is maintained, while the Phe$^8$ residue favors the trans conformation—an effect which is attributed to the avoidance of sidechain conformations which orient the methyl or the phenyl group gauche to both the carbonyl and amide groups (e.g. gauche(+)). In the 8S-(βMeF)SP analog, which is the least active of the monosubstituted analogs, the trans conformation is still favored at Phe[7], but the Phe[8] residue adopts the gauche(−) conformation. This suggests that a Phe[7]-trans, Phe[8]-trans conformation of the $3_{10}$ helical structure of SP may correspond to the conformation of SP which binds most effectively to the NK1 receptor. The 7S-(βMeF)SP analog, which is slightly more active than SP, favors such a trans, trans conformation approximately 87% of the time (according to the Boltzman distribution for the Phe[8] $\chi_1$ angle), and this analysis suggests that the high activity of this trans, trans conformation is diminished by its existing in the trans, gauche(−) conformation 13% of the time. Similarly, the 7R-(βMeF)SP analog, which is equipotent to SP, favors the Phe[7]-trans, Phe[8]-gauche (−) conformation 80% of the time, and if one assumes that the trans, trans conformation of this analog, which exists 20% of the time, is a highly active conformation (as suggested above), then one may infer that the low activity of the major trans, gauche(−) conformation is compensated for by the high activity of the minor trans, trans conformation. This simplistic analysis does not take into account subtle effects of the βMeF sidechains upon the backbone conformations of the monosubstituted SP analogs, but the superimposed structures indicated in FIG. 6 support the notion that an orientation of the Phe[8] sidechain corresponding to the trans conformation, in a $3_{10}$ helical structure, of substance P is necessary for effective binding to NK1, as the three analogs which are active (8R-, 7S-, and 7R-(βMeF)SP) all possess structures which project the Phe[8] phenyl ring in the same region of space, relative to the helical backbone, as the Phe[8]-trans form of the $3_{10}$ helical SP structure, while the less active 8S-(βMeF)SP analog projects its Phe[8] phenyl ring in a different region of space. The $^1$H-NMR studies of the monosubstituted SP analogs reported in this study agree with the molecular modeling results. In particular, the 8R-, 8S-, and 7R-(βMeF) SP analogs all exhibit large $J_{\alpha,\beta}$ coupling constants corresponding to these hydrogens being anti to each other, while the 7S-(βMeF)SP analog exhibited a small $J_{\alpha,\beta}$ coupling constant corresponding to the two hydrogens being gauche to each other.

A conformational analysis of the disubstituted βMeF-containing SP analogs similar to that discussed above for the monosubstituted analogs does not submit to any simple trends, but the concept, expressed above, that the Phe[8] phenyl ring must project out from the helical backbone in an orientation which corresponds to the Phe[8]-trans form of helical SP is nevertheless supported. The two most active disubstituted SP analogs, 7S,8S-(βMeF)$_2$SP and 7R,8S-(βMeF)$_2$SP, favor the Phe[7]-trans, Phe[8]-gauche(−) and Phe[7]-gauche(−), Phe[8]-gauche(−) conformations, respectively, which would not be expected to correspond to "active" conformations, according to the analysis employed above for the monosubstituted SP analogs. Furthermore, the equipotent (to SP) analog, 7S,8R-(βMeF)$_2$SP, and the least active analog, 7R,8R-(βMeF)$_2$SP, each favor the trans, trans conformations associated with high activity in the monosubstituted analogs. A possible solution to this dilemma can be found by accounting for the significant steric repulsions caused by placing two of the bulky, branched βMeF residues side-by-side in these disubstituted SP analogs. Such repulsions, which would be between the adjacent βMeF sidechains and/or between the βMeF sidechains and the C- or N-terminal portions of the peptide, could be anticipated to cause distortions in the backbone of the peptide significant enough to alter the shape of the peptide, even though the $3_{10}$ helix is maintained. The modeling studies were not capable of quantitating these subtle effects, but the minimized structures of the disubstituted analogs, indicated in FIG. 6 superimposed on the Phe[8]-trans conformation of the $3_{10}$ helical structure of SP (with the Phe[8] phenyl rings highlighted) do indicate that the disubstituted analogs maintain an overall shape which corresponds to that of substance P and that those disubstituted analogs which present their Phe[8] phenyl rings in a region of space which corresponds to the same region of space as that of the phenyl ring of the Phe[8] residue of SP are active, while those analogs which do not project their Phe[8] phenyl rings in that region are not active.

These studies indicate that 1) the introduction of either R-β-MeF or S-β-MeF residues into position 7 of SP does not significantly alter the biological activity, relative to SP, because it does not significantly alter the overall conformation of SP; 2) the introduction of R-β-MeF into position 8 of SP results in a four-fold enhancement of the biological activity, because it apparently helps to bias the sidechain conformation to an optimal trans conformation with respect to the Phe[8] $\chi_1$ dihedral angle while not significantly altering the peptide backbone conformation; 3) the introduction of S-β-MeF into position 8 of SP results in a ten-fold reduction of activity, because it apparently biased the sidechain conformation to a nonoptimal gauche(−) sidechain conformation while not significantly altering the peptide backbone conformation; and 4) the introduction of β-MeF residues into both positions 7 and 8 of SP cause steric interactions between the two sidechains of the β-MeF residues, resulting in alterations of the backbone conformations of the peptide which diminish the biological activity by a factor of ten in the case of the 7R,8R-(β-MeF)$_2$SP analog, do not significantly alter the activity in the case of the 7S,8R-(β-MeF)$_2$SP analog, and which enhance the activity in the cases of the 7R,8S-(β-MeF)$_2$SP and the 7S,8S-(β-MeF)$_2$SP analogs.

The addition of a single methyl group to the sidechain of the 8F residue of SP has been shown to significantly affect the interaction of the peptide with the NK1 receptor, as measured by rabbit iris sphincter contraction. Although a similar addition on Phe 7 yields an analog with similar activity as SP, the activities of the disubstituted analogs, along with molecular modeling studies, suggest that the methyl substitutions at Phe 7 result in an alteration of the backbone conformation, with the result (in some cases) that biological activity is maintained because the phenyl group on phenylalanine 8 can still occupy the same region of space as in SP, although it is held there from a different backbone scaffold. These results support the idea that the structure of SP in SDS micelles, as determined by Hicks, is a good representation of the conformation of SP which activates the NK1 receptor. The receptor appears to tolerate some variations in the peptide's backbone conformation as long as the phenyl groups, especially that on phenylalanine 8, is present in a proper region of space.

Although the foregoing invention has been described in detail for purposes of clarity of understanding, it will be obvious that certain modifications may be practiced within the scope of the appended claims.

What is claimed is:

1. A method for promoting healing of a vascular wound in a patient, said method comprising:
applying a composition to the wound in an amount sufficient to promote healing of the wound, wherein the composition comprises substance P or at least one analog thereof which comprises SEQ ID NO: 8 and a polymeric delivery vehicle selected from the group consisting of hyaluronic acid, methylcellulose, carboxymethylcellulose, hydroxymethylcellulose, hydroxypropylcellulose, hydroxyethylcellulose, collagen, and glycerin; and
wherein the polymeric delivery vehicle present in the composition increases the dwell time of the substance P or at least one analog thereof comprising SEQ ID NO: 8 such that the number of administrations of the composition required for promoting healing of the wound in the patient is reduced when compared to the number of administrations required for substance P or at least one analog thereof alone.

2. The method of claim 1, wherein the vascular wound is selected from the group consisting of burns, decubitus ulcers, venous stasis ulcers, and diabetic ulcers.

3. The method of claim 1, wherein the substance P or at least one analog thereof is present at a concentration in a range of from about 0.1 nM to about 1 mM.

* * * * *